United States Patent
Cushner et al.

(10) Patent No.: US 10,548,463 B2
(45) Date of Patent: Feb. 4, 2020

(54) IN-LINE GAS ADAPTOR FOR ENDOSCOPIC APPARATUS

(71) Applicant: UNITED STATES ENDOSCOPY GROUP, INC., Mentor, OH (US)

(72) Inventors: Jeffrey B. Cushner, Woodmere, NY (US); Christopher R. Stebbins, Huntington Station, NY (US); Kenneth E. Wolcott, Centerport, NY (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 361 days.

(21) Appl. No.: 15/489,314

(22) Filed: Apr. 17, 2017

(65) Prior Publication Data

US 2017/0215703 A1 Aug. 3, 2017

Related U.S. Application Data

(63) Continuation of application No. 13/874,568, filed on May 1, 2013, now Pat. No. 9,622,647, which is a
(Continued)

(51) Int. Cl.
*A61B 1/00* (2006.01)
*A61B 1/015* (2006.01)

(52) U.S. Cl.
CPC ...... *A61B 1/00119* (2013.01); *A61B 1/00112* (2013.01); *A61B 1/00121* (2013.01); *A61B 1/00128* (2013.01); *A61B 1/015* (2013.01)

(58) Field of Classification Search
CPC . A61B 1/00119; A61B 1/00128; A61M 39/10
(Continued)

(56) References Cited

U.S. PATENT DOCUMENTS

| 1,034,170 A | 7/1912 | Vanier |
| D189,383 S | 11/1960 | Macomber |

(Continued)

FOREIGN PATENT DOCUMENTS

| DE | 3324730 A1 | 1/1984 |
| EP | 0437229 A1 | 7/1911 |

(Continued)

OTHER PUBLICATIONS

Office Action for U.S. Appl. No. 12/424,211 dated Apr. 23, 2012.
(Continued)

*Primary Examiner* — Alexandra L Newton
*Assistant Examiner* — Rynae Boler
(74) *Attorney, Agent, or Firm* — Calfee, Halter & Griswold LLP

(57) ABSTRACT

The present invention provides an adaptor that is suitable for attachment to an endoscopic device for delivery of a secondary gas. The adaptor can comprise a substantially cylindrical body with a two, opposing closed ends, two fluid transport channels extending through the cylindrical body and opening at the closed ends, and an inlet port extending outward from the cylindrical body and being in fluid connection with one of the fluid transport channels. The adaptor may be used in endoscopy methods and is particularly useful for adding a secondary gas source in an endoscopy procedure.

16 Claims, 12 Drawing Sheets

Related U.S. Application Data continuation of application No. 12/881,683, filed on Sep. 14, 2010, now Pat. No. 8,454,499.

(60) Provisional application No. 61/242,121, filed on Sep. 14, 2009.

(58) Field of Classification Search
USPC ..... 600/154, 159; 604/164.02, 533, 537–539
See application file for complete search history.

(56) References Cited

U.S. PATENT DOCUMENTS

| | | | |
|---|---|---|---|
| 3,135,412 | A | 6/1964 | Cornelius |
| 3,222,135 | A | 12/1965 | Ashmead |
| 3,390,897 | A | 7/1968 | Buell |
| D227,558 | S | 7/1973 | Matthews, Jr. |
| 4,108,172 | A | 8/1978 | Moore, Jr. |
| 4,258,721 | A | 3/1981 | Parent et al. |
| 4,261,343 | A | 4/1981 | Ouchi et al. |
| 4,261,345 | A | 4/1981 | Yamaguchi |
| 4,262,671 | A | 4/1981 | Kersten |
| 4,311,134 | A | 1/1982 | Mitsui et al. |
| 4,325,362 | A | 4/1982 | Ouchi et al. |
| 4,350,647 | A | 9/1982 | De la Cruz |
| D271,618 | S | 11/1983 | Nishigaki |
| 4,464,316 | A | 8/1984 | Michaels |
| 4,474,574 | A | 10/1984 | Wolfe et al. |
| 4,489,712 | A | 12/1984 | Ohshima |
| 4,494,252 | A | 1/1985 | Chaoui |
| D280,206 | S | 8/1985 | Ishii |
| 4,538,593 | A | 9/1985 | Ishii |
| 4,539,586 | A | 9/1985 | Danna et al. |
| 4,548,197 | A | 10/1985 | Kinoshita |
| 4,550,716 | A | 11/1985 | Kinoshita |
| 4,552,130 | A | 11/1985 | Kinoshita |
| 4,637,378 | A | 1/1987 | Sasa |
| 4,667,655 | A | 5/1987 | Ogiu et al. |
| 4,691,701 | A | 9/1987 | Williams |
| 4,701,159 | A | 10/1987 | Brown et al. |
| 4,708,126 | A | 11/1987 | Toda et al. |
| 4,748,970 | A | 6/1988 | Nakajima |
| 4,760,838 | A | 8/1988 | Fukuda |
| D299,538 | S | 1/1989 | Balding et al. |
| 4,800,869 | A | 1/1989 | Nakajima |
| 4,844,052 | A | 7/1989 | Iwakoshi et al. |
| 4,901,142 | A | 2/1990 | Ikuno et al. |
| 4,905,852 | A | 3/1990 | Zumbuhl |
| 4,968,309 | A | 11/1990 | Anderson |
| 5,027,791 | A | 7/1991 | Takahashi |
| 5,054,481 | A | 10/1991 | Shin |
| 5,083,459 | A | 1/1992 | Cho et al. |
| 5,125,915 | A | 6/1992 | Berry et al. |
| 5,133,336 | A | 7/1992 | Savitt et al. |
| 5,163,576 | A | 11/1992 | Galer |
| 5,192,439 | A | 3/1993 | Roth et al. |
| 5,297,537 | A | 3/1994 | Savitt et al. |
| 5,309,906 | A | 5/1994 | LaBombard |
| 5,343,855 | A | 9/1994 | Iida et al. |
| 5,402,770 | A | 4/1995 | Iida et al. |
| 5,607,391 | A | 3/1997 | Klinger et al. |
| 5,630,795 | A | 5/1997 | Kuramoto et al. |
| 5,634,880 | A | 6/1997 | Feldman et al. |
| 5,697,888 | A | 12/1997 | Kobayashi et al. |
| D392,046 | S | 3/1998 | Niedospial, Jr. |
| 5,810,718 | A | 9/1998 | Akiba et al. |
| 5,830,128 | A | 11/1998 | Tanaka |
| 5,871,111 | A | 2/1999 | Pfefferkom et al. |
| 5,902,264 | A | 5/1999 | Toso et al. |
| 5,902,413 | A | 5/1999 | Puszko et al. |
| 6,189,870 | B1 | 2/2001 | Withall |
| 6,210,322 | B1 | 4/2001 | Byrne |
| 6,220,482 | B1 | 4/2001 | Sinnel et al. |
| 6,391,000 | B1 | 5/2002 | Belikan et al. |
| 6,394,000 | B1 | 5/2002 | Belikan et al. |
| 6,485,412 | B1 | 11/2002 | Byrne |
| 6,485,684 | B1 | 11/2002 | Mapson et al. |
| 6,558,317 | B2 | 5/2003 | Takahashi et al. |
| 6,575,160 | B1 | 6/2003 | Volgyesi |
| 6,575,946 | B2 | 6/2003 | Sealfon |
| 6,702,738 | B2 | 3/2004 | Ito |
| 6,764,442 | B2 | 7/2004 | Ota |
| 6,840,902 | B2 | 1/2005 | Sano et al. |
| 6,855,109 | B2 | 2/2005 | Obata et al. |
| 6,860,516 | B2 | 3/2005 | Ouchi et al. |
| 6,984,204 | B2 | 1/2006 | Akiba |
| 7,006,177 | B2 | 6/2006 | Pittaway et al. |
| 7,347,355 | B2 | 3/2008 | Sato et al. |
| 7,399,273 | B2 | 7/2008 | Moriyama et al. |
| 7,568,735 | B2 | 8/2009 | Akiba |
| 7,578,294 | B2 | 8/2009 | Pierro et al. |
| 7,582,056 | B2 | 9/2009 | Noguchi et al. |
| 7,597,662 | B2 | 10/2009 | Litscher et al. |
| D612,496 | S | 3/2010 | Bennison |
| 7,678,044 | B2 | 3/2010 | Fujikura |
| 7,766,898 | B2 | 8/2010 | Mottola et al. |
| 7,806,850 | B2 | 10/2010 | Williams, Jr. et al. |
| 7,824,329 | B2 | 11/2010 | Aizenfeld et al. |
| 7,837,769 | B2 | 11/2010 | Lahr |
| 7,892,223 | B2 | 2/2011 | Geiselhart |
| 7,901,350 | B2 | 3/2011 | Yamazaki |
| 7,914,519 | B2 | 3/2011 | Moran et al. |
| D639,940 | S | 6/2011 | Cushner et al. |
| 7,963,914 | B2 | 6/2011 | Uchimura et al. |
| D652,923 | S | 1/2012 | Kennedy et al. |
| 8,152,716 | B2 | 4/2012 | Aizenfeld et al. |
| 8,454,498 | B2 | 6/2013 | Cushner et al. |
| 2001/0044594 | A1 | 11/2001 | Martin et al. |
| 2003/0018238 | A1* | 1/2003 | Obata ............... A61B 1/12 600/179 |
| 2003/0032860 | A1 | 2/2003 | Avni et al. |
| 2003/0032862 | A1 | 2/2003 | Ota |
| 2003/0045779 | A1 | 3/2003 | Ito |
| 2003/0073971 | A1 | 4/2003 | Saker |
| 2004/0153047 | A1 | 8/2004 | Blank et al. |
| 2004/0199052 | A1 | 10/2004 | Banik et al. |
| 2004/0260151 | A1 | 12/2004 | Akiba |
| 2005/0263480 | A1 | 12/2005 | Smolko et al. |
| 2006/0052663 | A1 | 3/2006 | Koitabashi |
| 2006/0052665 | A1 | 3/2006 | Aizenfeld et al. |
| 2006/0068360 | A1 | 3/2006 | Boulais |
| 2006/0106285 | A1 | 5/2006 | Boulais et al. |
| 2006/0135851 | A1 | 6/2006 | Yamazaki |
| 2006/0178648 | A1 | 8/2006 | Barron et al. |
| 2006/0229498 | A1 | 10/2006 | Kohno |
| 2006/0241348 | A1 | 10/2006 | Kohno |
| 2006/0266423 | A1 | 11/2006 | Akiba et al. |
| 2006/0276689 | A1 | 12/2006 | Litscher et al. |
| 2006/0293562 | A1 | 12/2006 | Uchimura et al. |
| 2007/0043261 | A1 | 2/2007 | Watanabe et al. |
| 2007/0043262 | A1 | 2/2007 | Levy et al. |
| 2007/0066866 | A1 | 3/2007 | Noguchi et al. |
| 2007/0129705 | A1 | 6/2007 | Trombley, III et al. |
| 2007/0145738 | A1 | 6/2007 | Akiba |
| 2007/0225566 | A1 | 9/2007 | Kawanishi |
| 2007/0238929 | A1 | 10/2007 | Aizenfeld et al. |
| 2007/0244363 | A1 | 10/2007 | Sano et al. |
| 2008/0132763 | A1 | 6/2008 | Isaacson |
| 2008/0154095 | A1 | 6/2008 | Stubkjaer et al. |
| 2008/0214895 | A1 | 9/2008 | Campos |
| 2008/0269560 | A1 | 10/2008 | Ito et al. |
| 2009/0032533 | A1 | 2/2009 | Kessell et al. |
| 2009/0143719 | A1 | 6/2009 | Loori et al. |
| 2009/0188919 | A1 | 7/2009 | Takanohashi |
| 2009/0209822 | A1 | 8/2009 | Ikeda |
| 2009/0260629 | A1 | 10/2009 | Yee et al. |
| 2009/0264705 | A1 | 10/2009 | Cushner et al. |
| 2009/0266357 | A1 | 10/2009 | Varis et al. |
| 2010/0022834 | A1 | 1/2010 | Noda et al. |
| 2011/0174822 | A1 | 7/2011 | Gasser et al. |
| 2011/0263939 | A1 | 10/2011 | Kaye et al. |
| 2011/0275945 | A1 | 11/2011 | Karla et al. |
| 2012/0209062 | A1 | 8/2012 | Qiao |
| 2013/0245377 | A1 | 9/2013 | Cushner et al. |
| 2014/0316204 | A1 | 10/2014 | Ofir et al. |

(56) References Cited

U.S. PATENT DOCUMENTS

| | | |
|---|---|---|
| 2014/0316205 A1 | 10/2014 | Bendele et al. |
| 2015/0080661 A1 | 3/2015 | Kaye et al. |
| 2015/0297063 A1 | 10/2015 | Wolcott et al. |

FOREIGN PATENT DOCUMENTS

| | | |
|---|---|---|
| EP | 0075153 A2 | 3/1983 |
| EP | 0082950 A2 | 7/1983 |
| EP | 0361086 A1 | 4/1990 |
| EP | 2428157 A1 | 3/2012 |
| JP | 62125501 U | 8/1987 |
| JP | 1099558 A | 4/1989 |
| JP | H01280437 A | 11/1989 |
| JP | 5168587 A | 7/1993 |
| JP | 5220103 A | 8/1993 |
| JP | 5337074 A | 12/1993 |
| JP | 79301 U | 2/1995 |
| JP | 8106052 A | 4/1996 |
| JP | 08112251 A | 5/1996 |
| JP | 9164113 A | 6/1997 |
| JP | 10099265 A | 4/1998 |
| JP | 10276963 A | 10/1998 |
| JP | 2001299685 A | 10/2001 |
| JP | 2002177205 A | 6/2002 |
| JP | 2003024266 A | 1/2003 |
| JP | 2003070731 A | 3/2003 |
| JP | 2003111721 A | 4/2003 |
| JP | 2003339619 A | 12/2003 |
| JP | 2004147833 A | 5/2004 |
| JP | 2004242877 A | 9/2004 |
| JP | 2004305758 A | 11/2004 |
| JP | 2005021710 A | 1/2005 |
| JP | 2005245668 A | 9/2005 |
| JP | 2005304780 A | 11/2005 |
| JP | 2006042874 A | 2/2006 |
| JP | 2006110215 A | 4/2006 |
| JP | 2006116000 A | 5/2006 |
| JP | 2006167064 A | 6/2006 |
| JP | 2006280536 A | 10/2006 |
| JP | 2007089623 A | 4/2007 |
| JP | 2007252834 A | 10/2007 |
| JP | 2007313047 A | 12/2007 |
| JP | 2008029742 A | 2/2008 |
| JP | 2010057728 A | 3/2010 |
| WO | 9314688 A1 | 8/1993 |
| WO | 2006109351 A1 | 10/2006 |
| WO | 2008122969 A1 | 10/2008 |
| WO | 2009129302 A1 | 10/2009 |

OTHER PUBLICATIONS

International Search Report and Written Opinion from PCT/US2017/025655 dated Sep. 12, 2017.
Endoscope Channel guide, Evis™ 40/140/240 & Exera™ 160-Series GI Endoscopes, Olympus America, Inc. (2003), 1 page.
E-Scope (endoscope sales/services), e-Scope, LLC Brochure, dated Jan. 16, 2008, 2 pages.
Periphery Accessories Programme, PENTAX Brochure (undated) 20 pages.
Communication for European Patent Application No. 09731691.3 dated Dec. 5, 2011, 4 pages.
Communication Pursuant to Article 94(3) EPC for Application No. 10749572.3; dated Nov. 29, 2013.
International Preliminary Report on Patentability for Application No. PCT/US2009/040655 dated Oct. 19, 2010.
International Search Report and Written Opinion for Application No. PCT/US2009/040655 dated Jun. 29, 2009.
International Search Report and Written Opinion for Application No. PCT/US2010/046805 dated Dec. 7, 2010.
International Preliminary Report on Patentability for Application No. PCT/US2010/046805 dated Mar. 15, 2012.
Written Opinion for Application No. PCT/US2010/046805 (undated).
International Search Report and Written Opinion from International Application No. PCT/US2010/048578 dated Jan. 28, 2011.
International Search Report and Written Opinion for Application No. PCT/US2013/032005 dated Jun. 18, 2013.
International Search Report for Application No. PCT/US2014/025948 dated Jul. 29, 2014.
Notice of Allowance for U.S. Appl. No. 12/424,211 dated Mar. 28, 2014.
Office Action for U.S. Appl. No. 12/881,683 dated Aug. 22, 2012.
Notice of Allowance for U.S. Appl. No. 12/881,683 dated Jul. 2, 2013.
Notice of Allowance for U.S. Appl. No. 14/301,747 dated Mar. 31, 2015.
Notice of Allowance for Design U.S. Appl. No. 29/335,421 dated Feb. 10, 2011.
Office Action for U.S. Appl. No. 12/869,683 dated Aug. 16, 2012.
U.S. Appl. No. 12/869,265, filed Aug. 26, 2010; In re: Cusher et al; entitled In-Line Apparatus Gas Adaptor for Endoscpic Apparatus.
Notice of Allowance for U.S. Appl. No. 12/869,265 dated Feb. 4, 2013.
Restriction Requirement for U.S. Appl. No. 13/874,568 dated Jan. 14, 2015.
Amendment for U.S. Appl. No. 13/874,568 dated Mar. 5, 2015.
Office Action for U.S. Appl. No. 13/874,568 dated Mar. 26, 2015.
Amendment for U.S. Appl. No. 13/874,568 dated Jun. 22, 2015.
Office Action for U.S. Appl. No. 13/874,568 dated Jul. 30, 2015.
Amendment for U.S. Appl. No. 13/874,568 dated Sep. 30, 2015.
Advisory Action for U.S. Appl. No. 13/874,568 dated Oct. 15, 2015.
Amendment for U.S. Appl. No. 13/874,568 dated Oct. 29, 2015.
Office Action for U.S. Appl. No. 13/874,568 dated Jan. 29, 2016.
Amendment for U.S. Appl. No. 13/874,568 dated Apr. 29, 2016.
Office Action for U.S. Appl. No. 13/874,568 dated Aug. 12, 2016.
Amendment for U.S. Appl. No. 13/874,568 dated Nov. 14, 2016.
Notice of Allowance for U.S. Appl. No. 13/874,568 dated Dec. 5, 2016.
Notice of Decision of Granting Patent for Application No. 200980113305.0 dated Apr. 9, 2012.
Office Action for Canadian Application No. 2,772,341 dated Nov. 3, 2014.
Office Action for Chinese Application No. 200980113305.0 dated Nov. 16, 2011.
Office Action for Chinese Application No. 201080046225.0 dated May 4, 2014.
Office Action for European Application No. 09731691.3 dated Oct. 28, 2014.
Office Action for Japanese Patent Application No. 2011505165 dated May 31, 2013.
Office Action for Japanese Patent Application No. 2011505165 dated Sep. 21, 2012.
Office Action for U.S. Appl. No. 12/424,21 dated Oct. 5, 2012.
Office Action for U.S. Appl. No. 12/424,211 dated Dec. 4, 2013.
Office Action for U.S. Appl. No. 13/873,598 dated Jul. 30, 2015.
Office Action for U.S. Appl. No. 13/873,598 dated Mar. 26, 2015.
Office Action for U.S. Appl. No. 29/335,421 dated Dec. 7, 2010.
Office Action from U.S. Appl. No. 13/873,598 dated Nov. 16, 2015.
Office Action for U.S. Appl. No. 12/869,265 dated Aug. 16, 2012.
Office Action for Japanese Application No. 2012 526984; dated May 31, 2013.

* cited by examiner

IN-LINE GAS ADAPTOR FOR ENDOSCOPIC APPARATUS

CROSS-REFERENCE TO RELATED APPLICATIONS

This application is a continuation of U.S. application Ser. No. 13/874,568, filed May 1, 2013, which is a continuation of U.S. application Ser. No. 12/881,683, filed Sep. 14, 2010, now U.S. Pat. No. 8,454,499, issued Jun. 4, 2013, which claims priority to U.S. Provisional Application No. 61/242,121, filed Sep. 14, 2009, each of which is incorporated herein by reference in its entirety.

FIELD OF THE INVENTION

The present application is directed to devices used in surgical procedures, such as endoscopic procedures, and more particularly to a device that can be used to connect a secondary gas source to an apparatus, such as an endoscopic apparatus.

BACKGROUND

Many invasive medical procedures that previously required major surgery are now performed using endoscopic instruments. Such instruments can provide an internal view of particular body parts, organs, or passages without requiring invasive surgery. Generally, an endoscopic instrument may include one or more channels through which miniaturized, flexible instruments can be inserted and advanced. The endo scope typically includes an elongated flexible cable equipped at one end with an eyepiece or other viewing means and at the other end with an optical head. Only the head is directly and externally connected to the instrument. The cable transmits images or image-producing signals from the illuminated operative site to the viewing means to provide the instrument operator with full vision of the actions being performed at the instrument's working end. A coherent optic bundle extends from the head and through the flexible cable through the eyepiece for providing the surgeon with visual confirmation of the instrument's tip or jaw action. The illuminating means may take the form of a light-transmitting waveguide extending through the cable to illuminate the operative area. The waveguide is connected at its proximal end to a suitable high-intensity light source.

The cable of an endoscope also provides a flow passage for the delivery of fluid (e.g., liquid or gas) for irrigation or other purposes. Typically, the flow passage and the illuminating means are disposed on opposite sides of the coherent image-transmitting waveguide. In conventional practice, it is necessary to provide a flow of sterile water across the optic head to prevent the buildup of materials (e.g., surgical debris and body fluids) on the optic head. This flow of water operates, in a sense, like a windshield wiper/washer assembly.

In common designs, an endoscopic instrument typically has a control body which is connected by a light guide tube to a light guide connector, which actually can include a plurality of connectors that can suitably receive various fittings. For example, the light guide connector can include a connector orifice that receives a grounding lug, a suction port, an air inlet, and a water inlet. As such, the air and water are delivered through the light guide connector, through the light guide tube and into the control body. Alternatively, the control body can also include a water port so as to allow water to be directly provided to the control body. Suitable valves are provided on the control body so as to control the flow of water through the control body and over the optic head of the instrument.

For example, FIG. 1 illustrates an endoscope system that is unmodified (i.e., includes no secondary gas supply means). The endoscope is shown to include a shaft (insertion tube) connected to a control body that includes a biopsy port, air-water and suction valves, and angulation controls. The control body is connected to an umbilical (light guide connecting tube) that further connects to an electrical pin unit, which is directly connected to a light source and is connected via a video connection lead (and plug) to a video processor. The image produced by the endoscope is transmitted via a fiber optic bundle, or electronically from a charge-coupled device (CCD) chip. FIG. 1 illustrates a video monitor and attached keyboard for viewing images and inputting commands. The electrical pin unit includes a port for a water bottle connector that connects to a water bottle for providing irrigation.

The somewhat complex internal anatomy of the endoscope is further illustrated in FIG. 2, which shows a detailed view of the endoscope from FIG. 1. As seen in FIG. 2, the shaft incorporates an instrumentation channel extending from the entry biopsy port to the tip of the instrument. Channel sizes can vary from about 1 to 5 mm. Again, the endoscope includes no means for a secondary gas supply.

As seen in FIG. 1, the known practice has been to use a water bottle with a cap having a tube running therethrough. The tube typically has a fitting at the end distal to the bottle to allow for connection to the air/water connection port of the light guide connector (of the electrical pin unit, as illustrated in FIG. 1) or to the port on the endoscope control body. Typically, the tube connecting the water bottle to the endoscope is formed of an inner tube and an outer tube. The outer tube extends into the water bottle and is connected to the cap of the water bottle. In normal practice, air is delivered through the area between the inner tube and the outer tube so as to pressurize the interior of the water bottle and force water to flow through the tube and into the endoscope at a desired rate.

The known endoscopy assemblies have various limitations in relation to the provision of a gas source. For example, ambient air is often pumped into the system to charge the water bottle. It can be desirable, however, to use a secondary gas source instead of ambient air. Known devices allowing for substitution with a secondary gas source are excessively expensive. Moreover, known devices suffer problems associated with disinfection after each use. In practice, after usage, any fittings associated with the endoscopy device are sterilized, such as by glutaraldehyde disinfection and/or autoclaving. This creates a considerable expense to the hospital including the considerable labor expense associated with the disinfection of various parts and fittings. It also has not typically been feasible to simply dispose of various endoscopy fittings after a single use because of the previously noted expense associated with such parts.

Still further, the provision of a secondary gas source is complicated in that known endoscopy devices do not have universal, standardized connections. For example, the three main manufacturers of endoscopy devices (Olympus Optical Company, Ltd., Fujifilm Medical Systems, or its subsidiary, Fujinon Corporation, and Hoya Corporation, or its subsidiary, Pentax) each manufacture devices with an endoscope body that is universal to its own line of products but which is not suited for interchanging of parts between brands. Specifically, water bottle connectors for each manufacturer connect to the endoscope body via a different type of connection. Thus, there remains a need in the art for adaptors that allow for provision of a secondary gas in a manner that is economical and easy to use.

SUMMARY OF THE INVENTION

The present invention provides adaptors to improve the ease of provision and use of a secondary gas source in endoscopy. The inventive adaptors can be designed and shaped to function with endoscopic devices generally or may be designed and shaped to function with endoscopic devices having a particular structure unique to a single manufacturer of endoscopic devices. In light of their economical nature (and option for disposable, single use), the inventive adaptors allow for provision of a secondary gas in an endoscopy procedure without the requirement of costly, specialized equipment, such as a water bottle with a specially designed cap or a re-usable adaptor that has a much greater initial cost and must be sterilized between uses. These and other benefits of the present invention are more fully described herein.

In certain embodiments, the present invention provides adaptors that can be used with endoscopic devices. In particular, the adaptors can allow for the provision of a secondary gas to the endoscopic device via in-line placement between the endoscopic device and a water source connector.

In one embodiment, an adaptor according to the invention can comprise a substantially cylindrical body, the body being shaped and including specific structures to facilitate in-line attachment between an endoscope and a water source connector. For example, the cylindrical body can have a wall forming the sides of the cylinder, and the cylinder body can include two, opposing ends that are closed. The term closed can indicate that a structural component is present and is in contact with the cylinder wall at all points around the circumference thereof. As described below, certain further structural components can provide openings in the cylinder end, but this does not limit the closed nature of the cylinder since the formed openings provide for passages through the cylinder without necessarily providing an opening into the actual interior of the cylinder. Specifically, in embodiments wherein the cylinder includes open space therein, the cylinder remains closed because the openings formed in the ends of the cylinder do not allow for entry of fluid material into the open space in the cylinder, only passage through the cylinder without access to the cylinder interior (i.e., not contact with the interior surface of the cylinder walls). In specific embodiments, the adaptor can be described as comprising a substantially cylindrical body having a wall, a first closed end, and a second, opposing closed end.

As noted above, the inventive adaptor further may comprise one or more fluid transport channels. Such fluid transport channels may comprise a channel wall and can extend through the cylindrical body of the adaptor and open at the first and second closed ends of the cylindrical body. The presence of the channel walls prevents any fluid transported therethrough from actually entering any open space within the cylindrical body of the adaptor.

In light of the above, it can be seen that the adaptor can have a variety of separably definable components with walls. For example, the cylindrical body can have defined walls, a liquid channel extending end-to-end through the cylindrical body can have defined walls, and a gas channel extending end-to-end through the cylindrical body also can have defined walls. In some embodiments, two or more components may share a wall. For example, in one embodiment, a portion of the gas channel (or the gas channel wall) can form a portion of the cylindrical body wall. Likewise, the gas channel and the liquid channel could be in sufficiently close proximity that the walls of the two channels could be physically attached and could even be a single piece with two channels formed therein and two separate openings at each closed end of the cylindrical body. In another embodiment, one channel (e.g., the gas channel) could be formed within the cylindrical body wall. In other embodiments, the cylindrical body could be substantially solid, and the channels formed therein could be substantially the only free space within the cylindrical body.

In further embodiments, the adaptor can comprise an inlet port extending outward from the wall of the cylindrical body and having a central passage therein. Preferably, the passage extends through the wall of the cylindrical body and is in fluid connection with one of the first and second fluid transport channels. In other embodiments, the inlet port may be described as intersecting a wall of the adaptor body and/or intersecting the wall of one of the fluid transport channels to form an opening therein.

In preferred embodiments, the inlet port of the inventive adaptor may comprise a luer, barb, tapered, threaded, snap fitting, or conical connector. Such connectors are more fully described below. In specific embodiments, the luer connector may be in accordance with ISO 594-2:1998. In an alternative embodiment, the adapter may include an adhesive for coupling the inlet port to a connection associated with the secondary gas source.

The alignment of the inlet port in relation to the adaptor body can vary. Specifically, the inlet port could have any length or geometry (i.e., substantially straight, L-shaped, curved, or the like) useful to facilitate ease of attachment of a secondary gas source to the inlet port. In specific embodiments, the inlet port is substantially perpendicular to the wall of the cylindrical body of the adaptor. Thus, the attachment of the inlet port to the cylindrical body may be such that the exterior surfaces of the walls of the components are at about a 90° angle. Of course, such angle could vary as deemed useful. In some embodiments, the angle can be between about 10° and about 90°, between about 20° and about 90°, between about 30° and about 90°, between about 40° and about 90°, between about 45° and about 90°, between about 50° and about 90°, or between about 60° and about 90°. In specific embodiments, the length of the inlet port may be about 1 cm to about 5 cm, about 1.5 cm to about 4.5 cm, about 1.5 cm to about 4 cm, or about 1.5 cm to about 3 cm. Preferably, the alignment, shape, and length of the inlet port provide for ready access while the adaptor is inserted in-line between an endoscope control body and a water source connector. Component geometry also may be related to the fluid transport channels of the adaptor body. For example, the first and second fluid transport channels may be described as being substantially parallel. Moreover, they may be described as being in a side-by-side relation. As will be evident from the further disclosure herein, such alignment can be particularly useful to facilitate use with specific types of endoscope devices, and any adaptor not having such alignment or structure would be expressly excluded from being used in connection with the specific type of endoscope device. Specifically, in some embodiments, the inventive adaptor can be designed and shaped for attachment specifically to a Fujinon-manufactured endoscopic device. Such specificity can arise from the specific structure and placement of elements on the Fujinon-manufactured endoscope devices for delivery of fluid into the endoscope (such as from a water bottle). The adaptor of the present invention may be expressly structured for insertion in-line in a Fujinon-manufactured endoscope and water bottle connector assembly.

In specific embodiments, the fluid transport channels may be described in relation to the specific type of fluid to be transferred therethrough. For example, the first fluid transport component may be referred to as a liquid transport component. Similarly, the second fluid transport channel may be referred to as a gas transport component. Preferably, the inlet port included in the adaptor extends outward from the wall of the cylindrical body of the adaptor in a position wherein the inlet port is in fluid connection with the gas transport channel. Thus, the channel formed in the gas inlet port could pass through the wall of the cylindrical body and/or the wall of the gas transport channel.

Sizes and dimensions of specific portions of the inventive adaptor can be specifically determined for use with specific devices. For example, endoscope control bodies manufactured by Fujinon Corporation are known to include a fluid transport hub to facilitate transfer of water to and from a water bottle via attachment to a specifically formed receptacle in a water bottle connector. In certain embodiments, the inventive adaptor may be formed to specifically interact with such hub and receptacle.

For example, in one embodiment, the cylindrical body of the adaptor may comprise a flange in the proximity of one end (e.g., the first closed end). Specifically, the flange can comprise a flange wall that is substantially parallel to the wall of the cylindrical body. This structure particularly can be useful to provide means for receiving a fluid transport hub, which typically can be shaped substantially like the open end of a cylinder. The relationship of the flange wall to the wall of the cylindrical body of the adaptor thus can form an annular space that can be shaped specifically to receive the correspondingly shaped hub on an endoscope body, such as that manufactured by Fujinon Corporation. Moreover, the flange wall can include means to secure the engagement. Specifically, the hub may include a pin, and the flange wall may include means to receive such a pin in a sliding engagement. Such means could be, for example, a channel or slit formed in the flange wall.

In further embodiments, the cylindrical body wall of the inventive adaptor may comprise a flared extension at one end thereof. Specifically, this structure may extend beyond the end of the cylindrical body (e.g., beyond the second closed end). The flared extension specifically may comprise an exterior surface which can include at least one pin extending therefrom. Such pin can be particularly useful for engaging a securing receptacle formed in a water source connector.

Further to the above, the specifically shaped and designed ends of the cylindrical body may be shaped to facilitate a press-fit, sealed engagement with the fluid transport elements on the endoscopic device and/or the water source connector without secondary engaging means. This is particularly beneficial because of the ease of use of a press-fit adaptor and the ability to prepare such adaptors in a very cost-effective manner that allows passage of the cost savings on to an end-user. Moreover, the press-fit adaptor would be useful with an endoscopic device while avoiding fluid loss since known in-line devices typically include secondary means for securing the device, such as a screw collar or the like. While the present adaptor may be described in terms of a twist engagement, this merely relates to a twisting of the two components being connected to engage any retaining mechanism (e.g., fully engaging a pin with an angled or L-shaped slot) and does not require the use of an additional locking mechanism, such as a screw collar.

In light of the foregoing, it can be seen that the inventive adaptor can be described as being shaped in the proximity of the first closed end to engage a fluid transport element extending from a portion of an endoscopic device. Particularly, the adaptor can be shaped to facilitate a twist-fit, sealed engagement with the fluid transport element on the endoscopic device without secondary engaging means. Similarly, the adaptor can be shaped in the proximity of the second closed end to engage a water source connector. Particularly, the adaptor can be shaped to facilitate a twist-fit, sealed engagement with the water source connector without secondary engaging means.

In some embodiments, the adaptor further can comprise one or more sealing members. For example, a sealing member may be located at one or both of the closed ends of the cylindrical body. In one embodiment, the sealing member can be a gasket.

In some embodiments, the adaptor may be formed as a single item that is shaped to provide the individual components. Such nature of the inventive adaptor may arise from the method of formation of the adaptor and the material used to form the adaptor. Specifically, the adaptor may be formed of a polymeric material. As such, the adaptor may be described as being formed of a plastic material. In some embodiments, the polymeric material used to prepared an adaptor according to the invention may be a material that is chemical resistant, heat resistant, or both chemical resistant and heat resistant.

In one embodiment, the adaptor body may be described as being a single piece of polymeric material having two channels formed therein. Preferably, the two channels do not intersect and are not in fluid connection. One channel may be a liquid channel and the other channel may be a gas channel. Both channels preferably are linear and may be substantially or completely straight. The gas channel may be branched and may be described as being substantially T-shaped, one line extending the length of the adaptor (i.e., from one closed end of the cylindrical body to the opposing closed end) and the other line extending through the inlet port, for example, the second line extending substantially perpendicularly from the first line.

In light of the foregoing description, it is clear that the inventive adaptor also may be described in terms of the method of manufacture. For example, the adaptor, particularly the adaptor body, may be described as being a molded part.

Thus, in some embodiments, the invention also can provide a method of preparing an adaptor for secondary gas provision in an endoscope. The method can comprise providing a mold shaped to form an adaptor body that is a single, integral piece of polymeric material having two channels formed therein, injecting a polymer into the mold, and allowing the polymer to harden. Preferably, after the molding process, the edges of the adaptor body are free and clear of flashing and flecking. Further, preferably, the molding process is free of any mold release agent such that the molded part is free of any mold releasing agent. Moreover, preferably, the molding process is controlled such that the finished part is free and clear of any grease or other lubrication used in a molding tool.

In a particular embodiment, the present invention can provide an adaptor for an endoscopic device, the adaptor being defined in relation to its specific form. For example, the invention can encompass an adaptor that can be a monolithic, polymeric material formed as a substantially cylindrical body with closed ends and including two fluid transport channels extending through the cylindrical body and opening at the closed ends of the cylindrical body, one of the fluid transport channels being branched and forming an inlet port extending outward from the cylindrical body. Further structures as described herein also could be included with such an adaptor.

In another aspect, the invention can provide methods of carrying out an endoscopic procedure. In one embodiment, a method according to the invention can comprise using an assembly including an endoscopic device, a water source, a gas source, and an adaptor according to any embodiment disclosed herein.

In a specific embodiment, a method for supplying a secondary gas in an endoscopic procedure can comprise the following steps: using an endoscope device having attached thereto a water source with a connector; affixing between the water source connector and the endoscope device an adaptor according to the present invention; and supplying a secondary gas to the endoscope device via the gas inlet port on the adaptor. Specifically, the adaptor can comprise a substantially cylindrical body having a wall, a first closed end, and a second, opposing closed end; a first fluid transport channel having a channel wall and extending through the cylindrical body and opening at the first closed end and the second closed end; a second fluid transport channel having a channel wall and extending through the cylindrical body and opening at the first closed end and the second closed end; and an inlet port extending outward from the wall of the cylindrical body and having a central passage extending through the wall of the cylindrical body and being in fluid connection with one of the first and second fluid transport channels. Preferably, the secondary gas comprises carbon dioxide, although other gases or combinations of gases could be used.

BRIEF DESCRIPTION OF THE DRAWINGS

Figure 1:
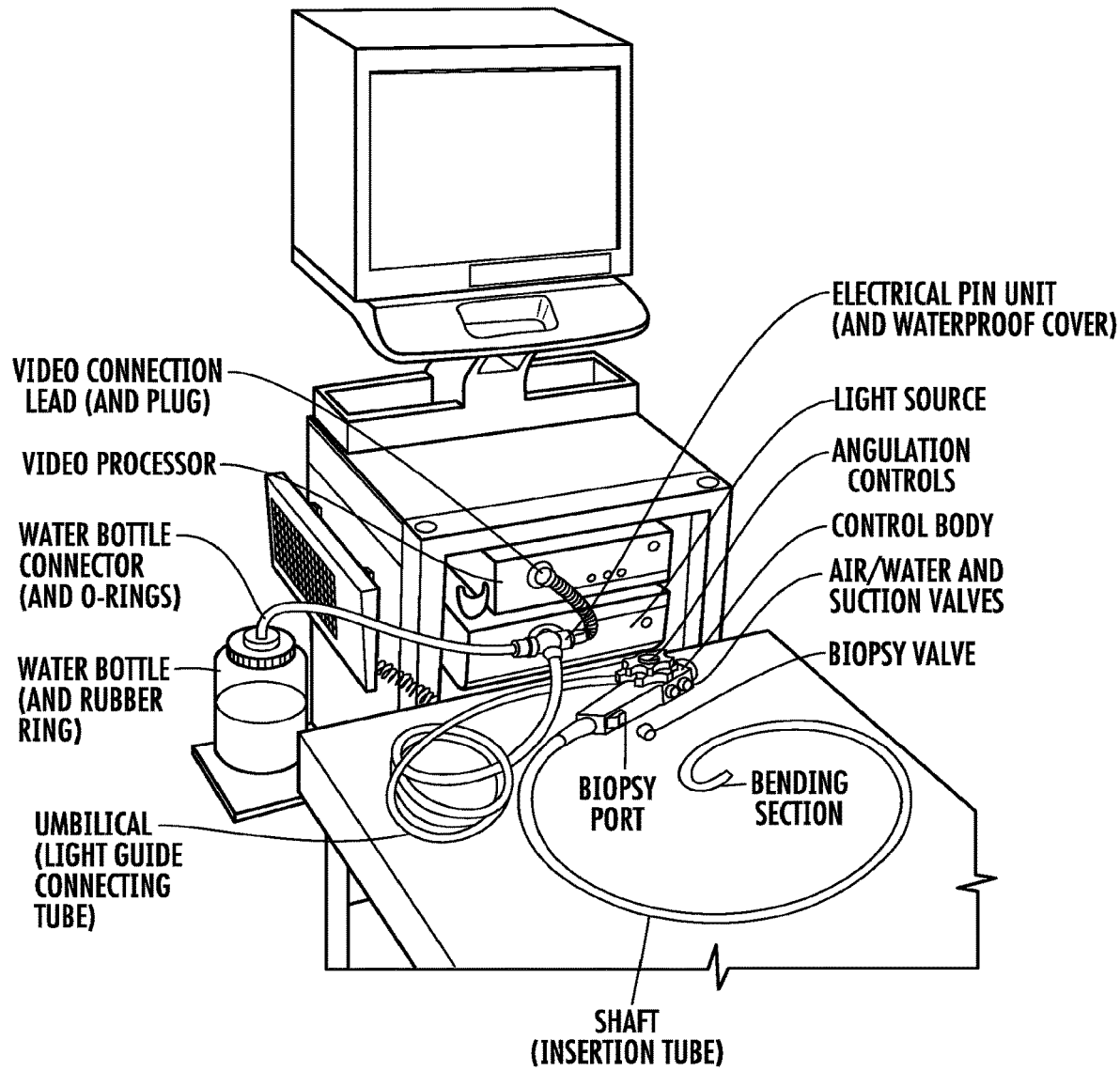
Figure 2:
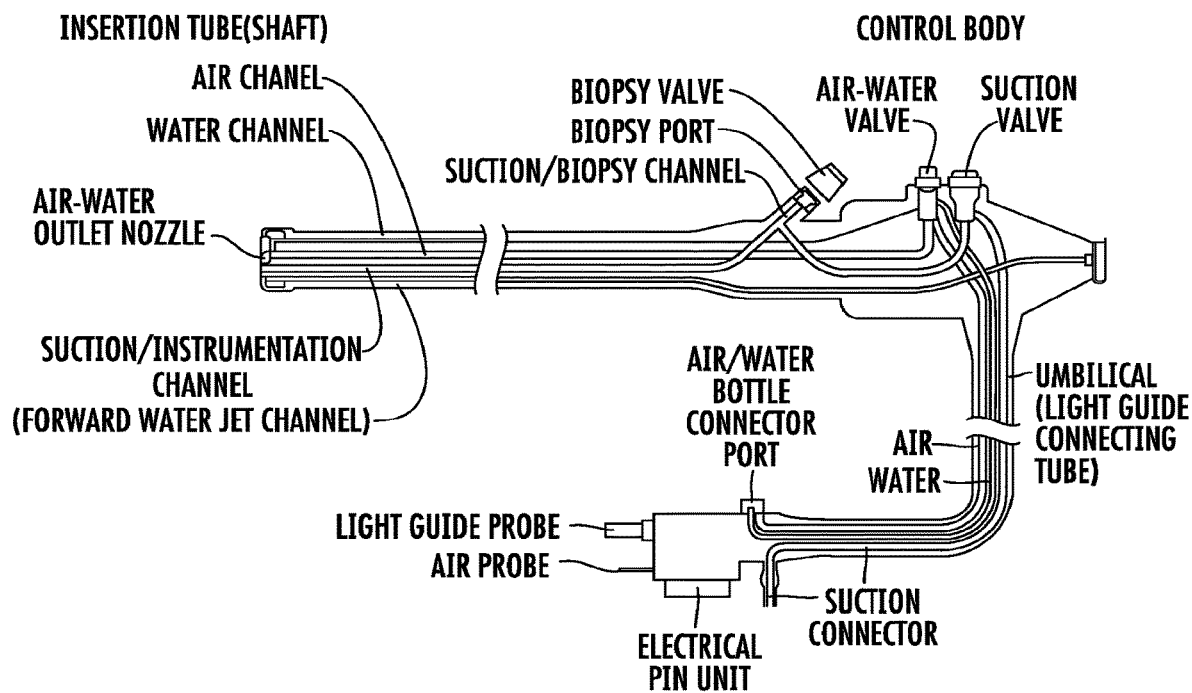
Figure 3:
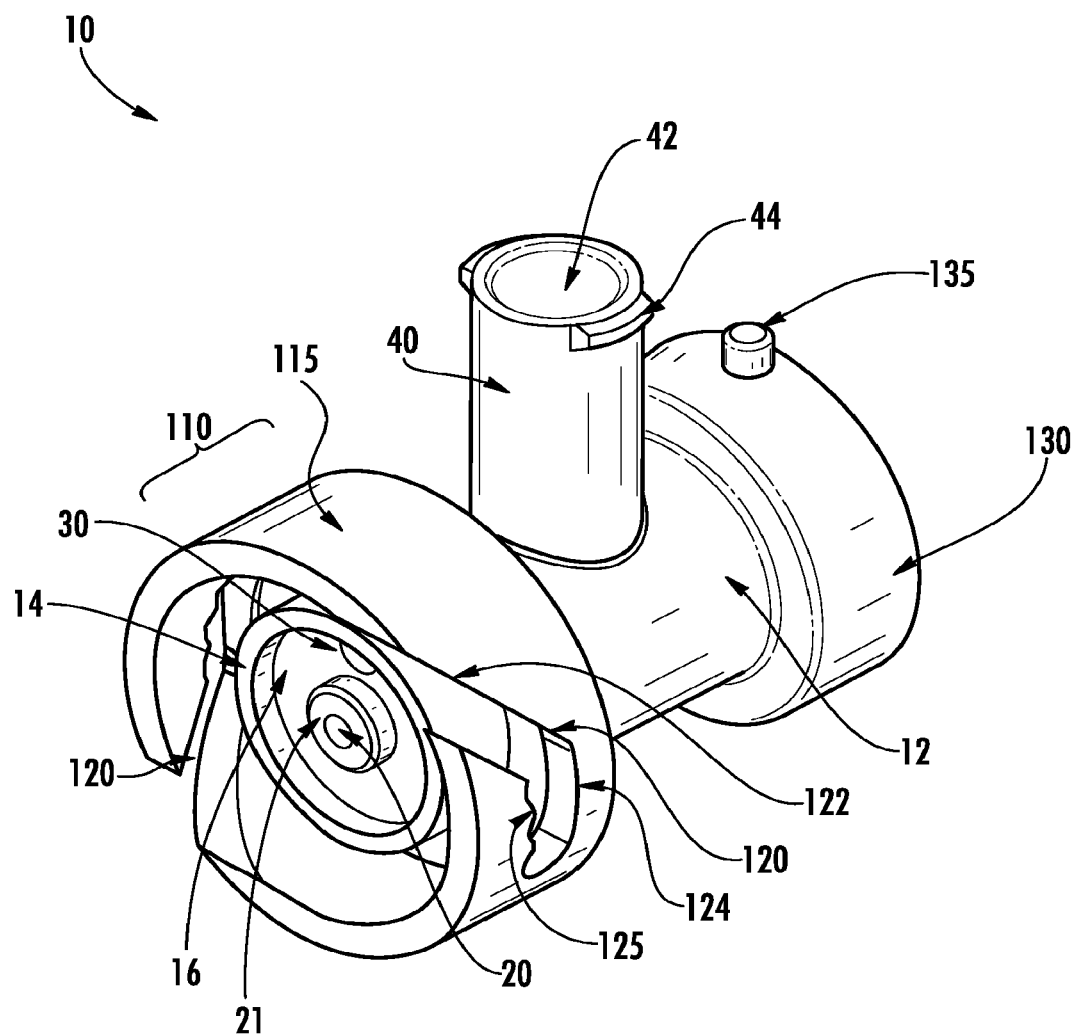
Figure 4:
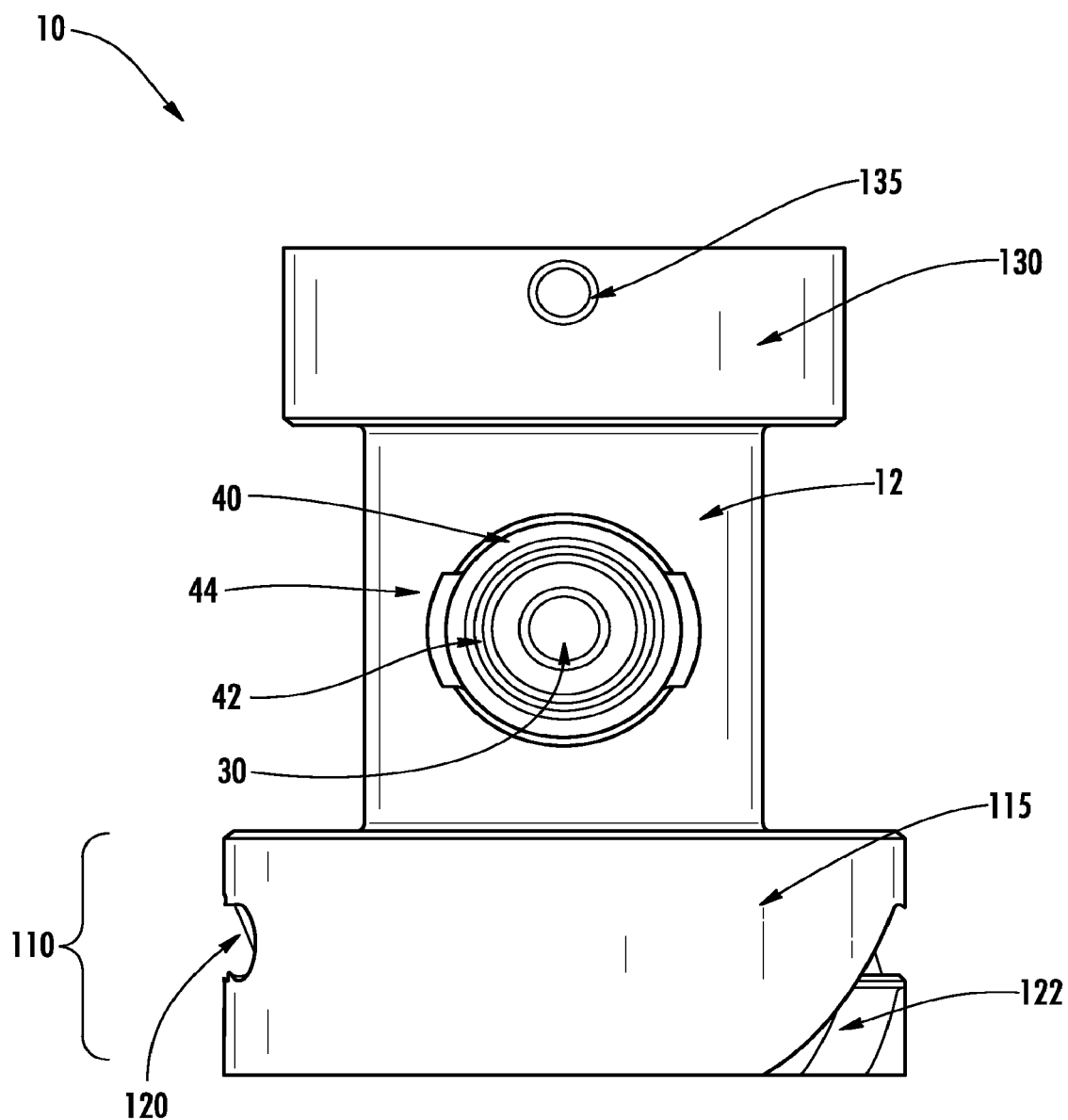
Figure 5:
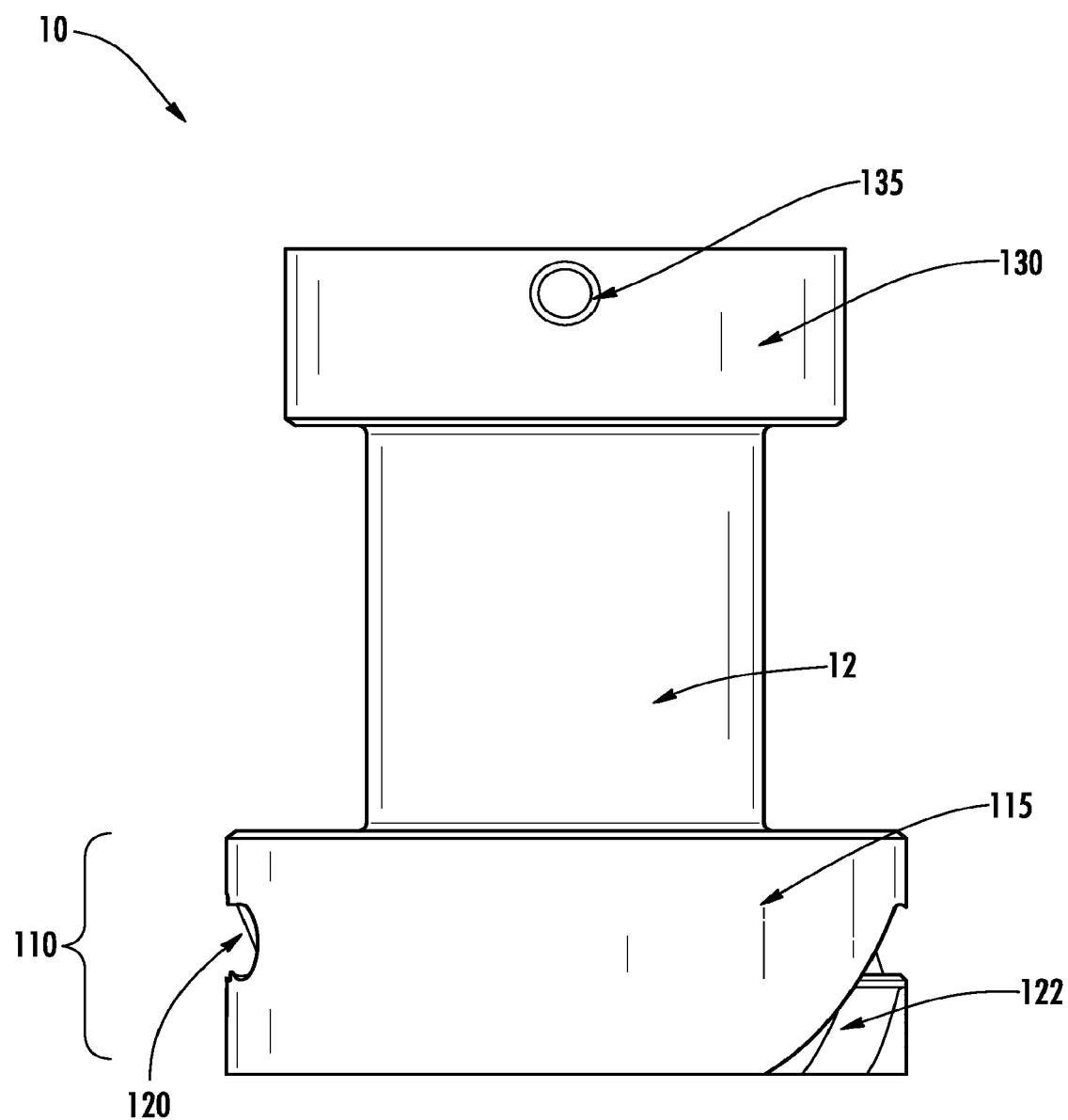
Figure 6:
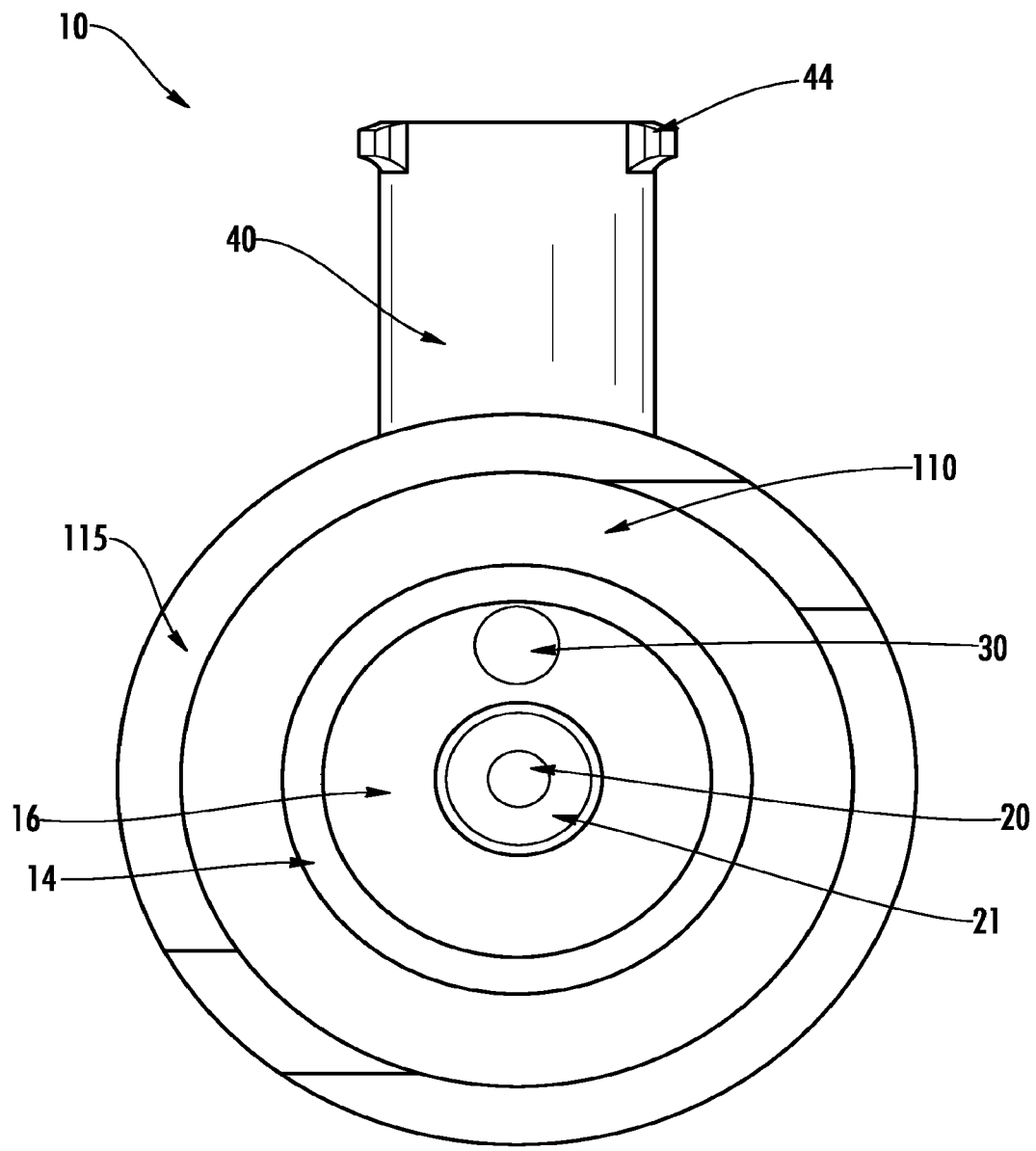
Figure 7:
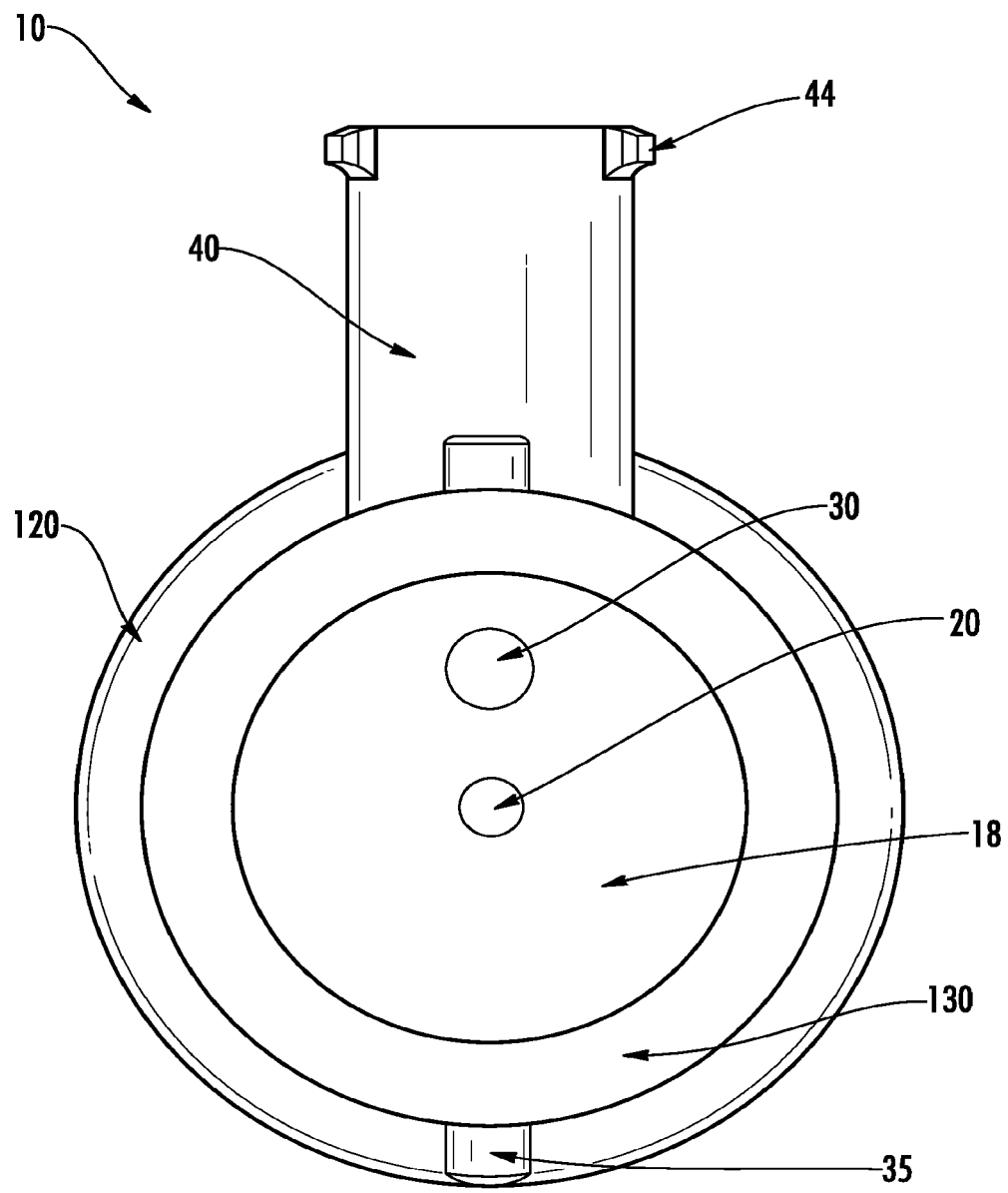
Figure 8:
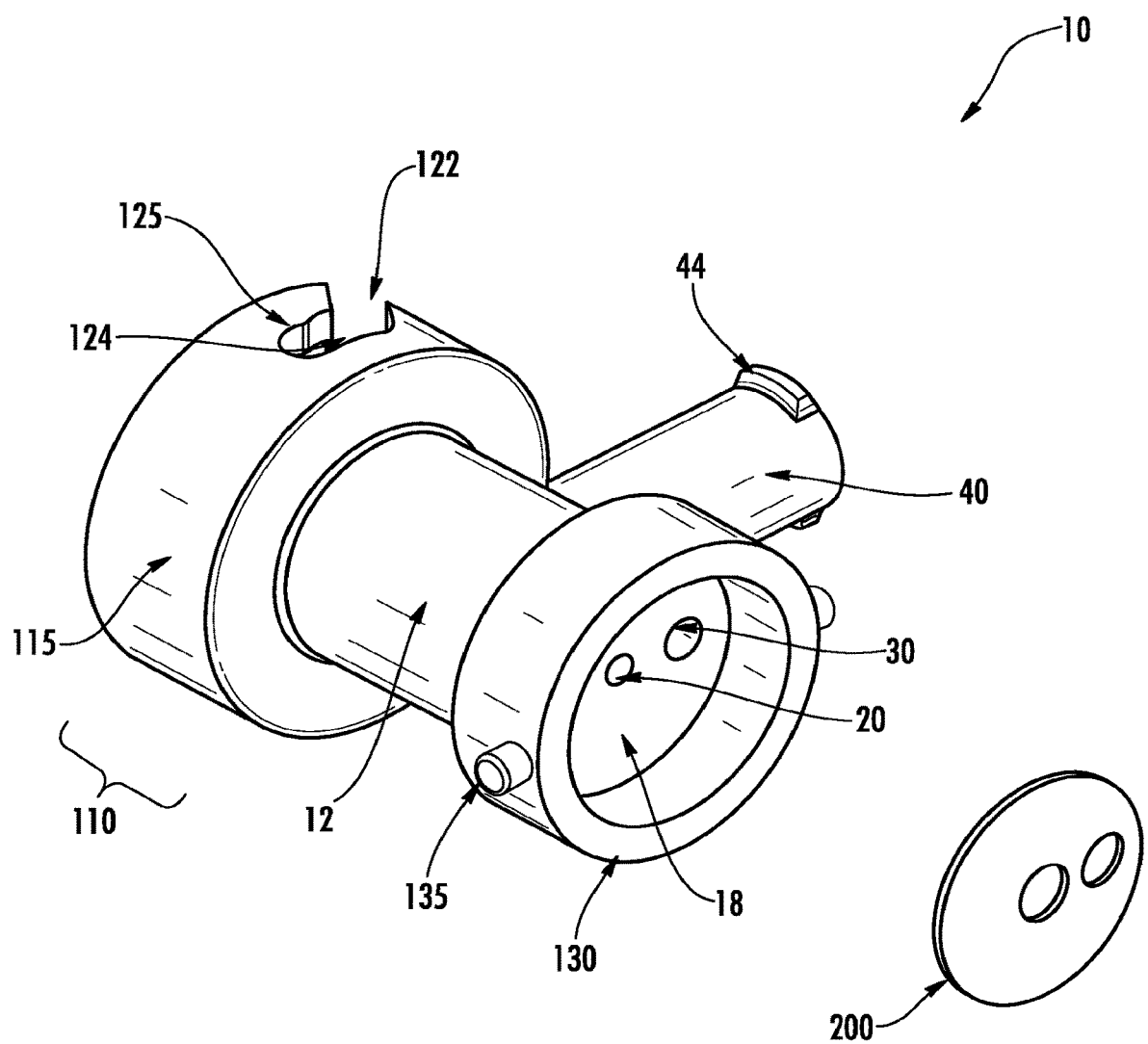
Figure 9:
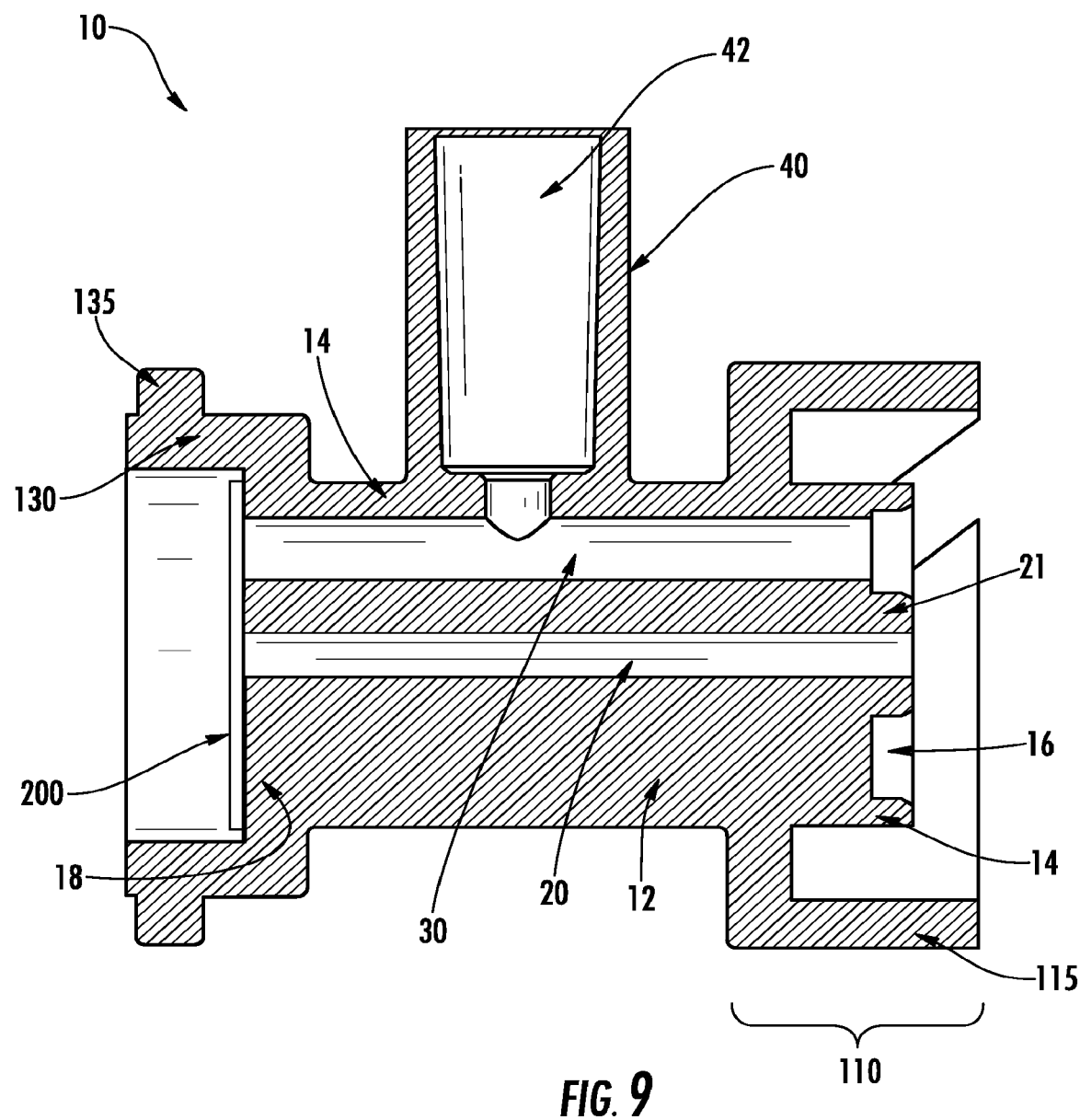
Figure 10:
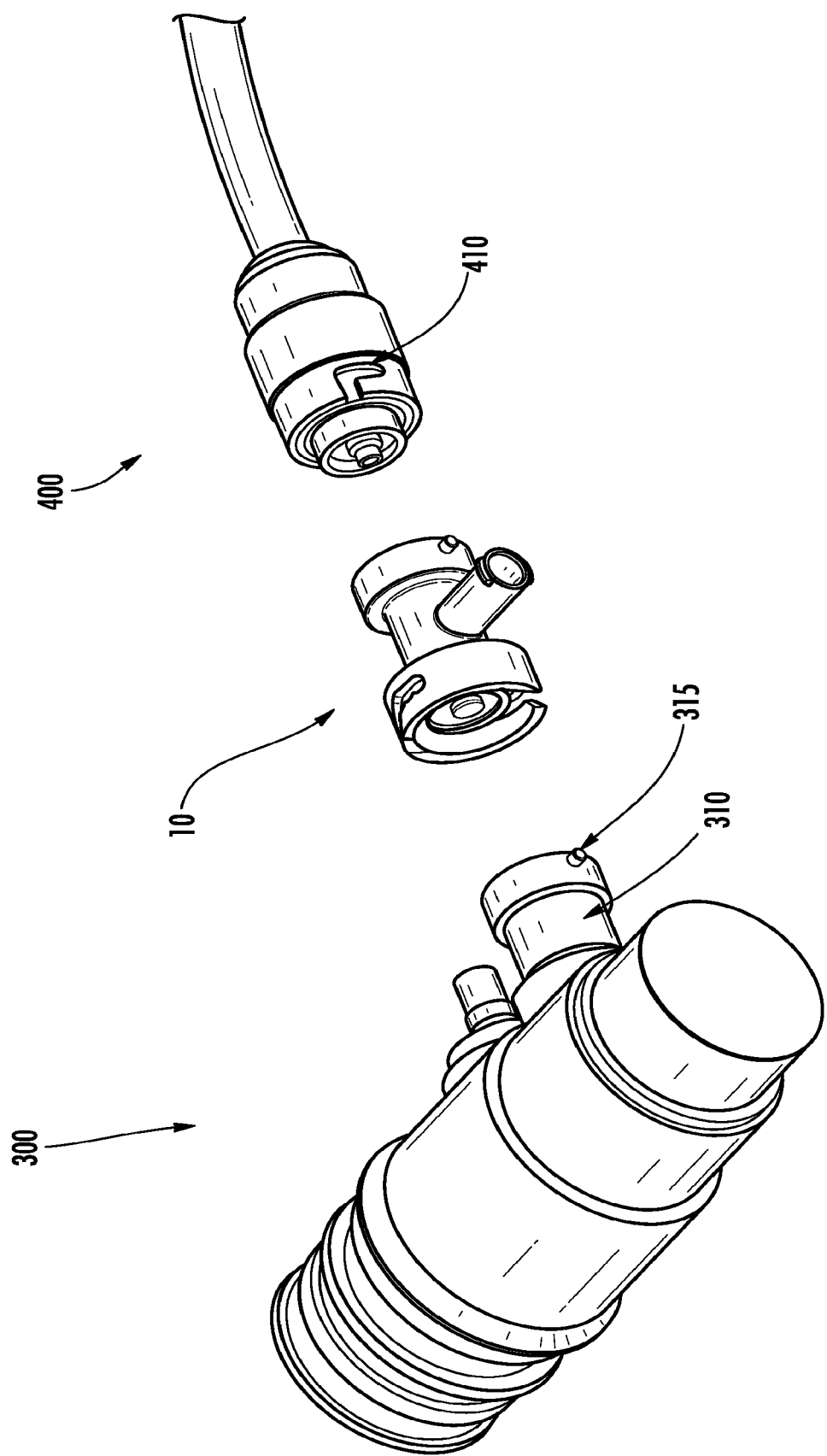
Figure 11:
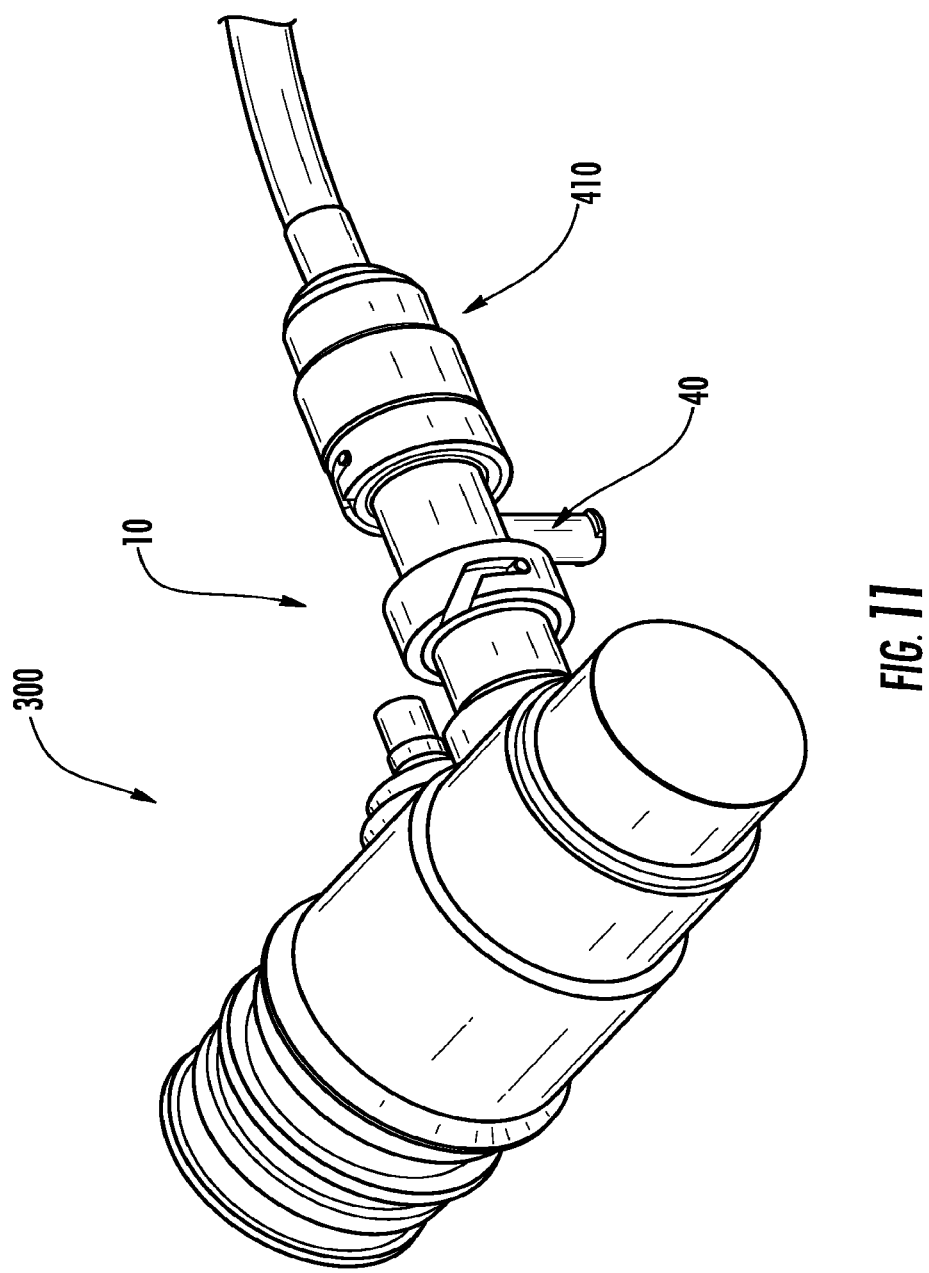
Figure 12:
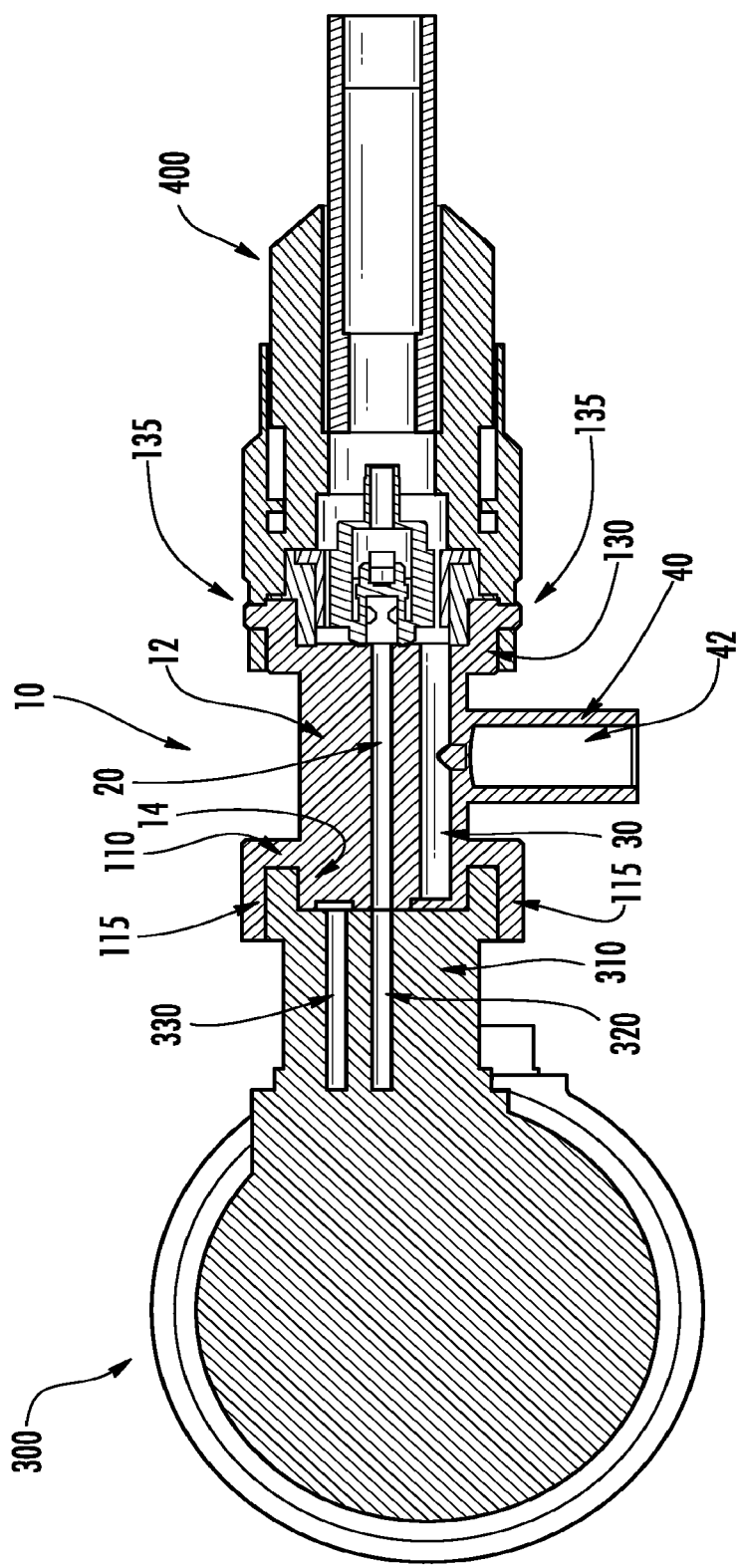

Having thus described the invention in general terms, reference will now be made to the accompanying drawings, which are not necessarily drawn to scale, and wherein:

FIG. 1 is an illustration of an unmodified endoscope system that includes no means of providing a secondary gas supply;

FIG. 2 is a detailed view of the endoscope from the system illustrated in FIG. 1;

FIG. 3 is a perspective view of an adaptor according to one embodiment of the invention;

FIG. 4 is a bottom view of an adaptor according to one embodiment of the invention;

FIG. 5 is a top view of an adaptor according to one embodiment of the invention;

FIG. 6 is a front view of an adaptor according to one embodiment of the invention;

FIG. 7 is a rear view of an adaptor according to one embodiment of the invention;

FIG. 8 is an exploded view of an adaptor according to one embodiment of the invention;

FIG. 9 is a cross-section of an adaptor according to one embodiment of the invention;

FIG. 10 is an exploded view showing an adaptor according to one embodiment of the present invention in position for placement in-line between a water source connector and the control body of an endoscope device;

FIG. 11 illustrates an adaptor according to one embodiment of the invention placed in-line between a water source connector and the control body of an endoscope device; and FIG. 12 is a cross-section showing the press fit, in-line attachment of an adaptor according to one embodiment of the invention placed between a water source connector and the control body of an endoscope device.

DETAILED DESCRIPTION

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention provides an adaptor that allows for the use of any secondary gas during an endoscopic procedure. Endoscopic assemblies typically include a water source, such as a water bottle. These often include caps that have a dual-lumen tube that supplies air through one lumen to charge the water bottle. This charge gas may be considered a primary gas. Any gas provided during an endoscopic procedure in addition to or in lieu of this charge gas may be considered to be a secondary gas according to the present invention. In one embodiment, the secondary gas is carbon dioxide.

Introduction of a gas into a body cavity is common practice in gastrointestinal endoscopic procedures. Previously, when it has been desired to introduce a gas during an endoscopic procedure, standard room air was simply introduced (such as from the light source). More recently it has been found that the use of carbon dioxide ($CO_2$) insufflation can improve post-procedure patient comfort since $CO_2$ is more easily absorbed by the body. For example, use of $CO_2$ may be particularly useful for long endoscopic exams, such as endoscopic retrograde cholangiopancreatogram (ERCP), enteroscopy, and colonoscopy, and gas may be used in other endoscopic procedures as well, such as endoscopic ultrasound (EUS) and esophagogastroduodenoscopy (EGD). Provision of a secondary gas source has proven challenging, however. For example, the addition of $CO_2$ in an endoscopic procedure has previously required the use of cumbersome external regulators, flow meters, and specialized valves. The advent of specialized equipment for the provision of a secondary gas in an endoscopic procedure, such as the $CO_2$EFFICIENT™ Endoscopic Insufflator (available from Bracco Diagnostics, Inc., Princeton, N.J.), has simplified secondary gas supply. Still, though, the lack of standardization in endoscopic devices made by different manufacturers continues to complicate the provision of a secondary gas in association with a variety of endoscopic devices. For example, Pentax has available a gas adaptor that is designed exclusively for its endoscopic devices. The Pentax adaptor, though, is relatively expensive, is designed for multiple uses, and can be difficult to use (for example requiring attachment via a screw collar). This design raises the issues of cost and patient safety associated with the cleaning of reusable parts. Olympus and Fujinon have each addressed the provision of a secondary gas when using their respective endoscopic devices by providing water bottles with bottle caps that include some means for attaching a gas source. Again, the cost of these parts can be prohibitive and sterilization between uses is still required. In contrast, the present invention has made possible the addition of a secondary gas in a manner that is easy to use, medically safe, and economical.

The ability to use any secondary gas of choice according to the invention can be achieved through provision of an adaptor for use "in-line" with an endoscopic device. As discussed previously, endoscopic devices typically include a main body to which a number of different cord, tubes, or lines are attached. This provides for introduction of light, fluids, and instruments into the body of a patient. As used herein, the term "in-line" is understood to mean that the adaptor is designed to function with an endoscopic device by being positioned between two or more components of the device. Thus, "in-line" can mean that the adaptor is positioned between two or more of a main body, a cord, a tube, a line, a connector, or the like. A skilled person readily would be able to envision the different parts of an endoscopic device where an adaptor according to the invention would be positioned to provide the function described herein. In specific embodiments, an adaptor according to the invention is designed for positioning in-line between the main body of an endoscopic device and the cord, tube, or line leading to a water source. Specifically, the adaptor may connect at one end to the main body of the endoscopic device and at another end to a water bottle connector.

In one aspect, the present invention provides an adaptor for an endoscopic device. The adaptor particularly is designed to be positioned in-line with existing components of an endoscopic device. Such design is evident by the disclosure provided hereinafter.

In certain embodiments, the adaptor generally can be described in terms of a number of individual components. Such description can indicate that the adaptor is formed of a number of separate components that are combined to make the overall structure. In specific embodiments, though, the adaptor may be substantially a single, integral component. In other words, the adaptor may be a single, monolithic structure. In some embodiments, the adaptor may be a single, monolithic structure and may further comprise one or more additional components, as described below. In preferred embodiments, the adaptor may be characterized by its single, integral nature, such as the express lack of any movable parts needed to secure the adaptor to the remaining components of an endoscopic device. In specific embodiments, the adaptor may be described as being formed of a body, one or more fluid transport components, and an inlet port that together are a single, monolithic structure. The term monolithic is understood as meaning that the overall adaptor is a unitary structure having a seamless construction that cannot be separated into its individual components without the use of destructive means, such as cutting the components apart.

Although the adaptor body preferably exhibits a single, integral structure, the structure of the adaptor can be described in relation to the function and shape of the various components or areas of the adaptor. For example, in some embodiments, the adaptor may be described as having a body that has a specific shape. Particularly, the adaptor may have a substantially cylindrical body. Of course, the adaptor body is not necessarily limited to such geometry and could take on other cross-section shapes (e.g., a substantially square cross-section). As used in relation to the adaptor body shape, the word "substantially" is intended to define the shape in that it need not necessarily be geometrically perfect. In other words, a substantially cylindrical body could have a cross-section that is a circle, but the circle could be somewhat elongated or flattened. Thus, a substantially cylindrical shape is understood to provide a degree of variance from a cross-section that is a perfect circle.

The length of the substantially cylindrical body can vary. As will be more evident below, the adaptor typically will be placed in use between the main body of an endoscope and a water source connector, and the length of the adaptor body will affect the distance by which the water source connector is separated from the endoscope main body. Preferably, the length of the adaptor is minimized but will still allow for easy access to the inlet port on the adaptor and provide sufficient space for connection to the endoscope main body and the water source connector. In some embodiments the adaptor body may have a length of about 2 cm to about 8 cm, about 2 cm to about 7 cm, about 2 cm to about 6 cm, about 2 cm to about 5 cm, about 2 cm to about 4 cm, or about 2 cm to about 3 cm.

Connection of the adaptor body to the endoscope main body and the water source connector can be facilitated though the inclusion of specific structures on the adaptor body. The nature of these additional structures can be expressly designed in relation to the brand of endoscope. As noted previously, the three main manufacturers of endoscope devices make devices with significantly different structures. For example, a Pentax endoscope main body includes a connector with one or two pins extending from the outer surface of the connector. A water source connector for a Pentax endoscope thus includes a slit for receiving the pin. The inventive adaptor can be similarly designed.

In one embodiment, the adaptor body may include a flange in the proximity of one of the ends of the adaptor body. This flange particularly may include a wall that is substantially parallel to the wall of the adaptor body. The parallel wall thus may include means for receiving a pin in a sliding engagement. Such means may be a groove, slit, channel, passage or similar opening that may be engaged by a pin or like element. The flange may be in the proximity of the adaptor body end such that the flange attaches to the wall of the adaptor body at some distance behind the adaptor body end. Moreover, the parallel wall of the flange may have a length sufficient so that the parallel wall terminates beyond the end of the adaptor body. For example, in an embodiment wherein the flange attaches to the adaptor body approximately 5 mm from the end of the adaptor, the parallel wall of the flange preferably would have a length of at least about 6 mm. In specific embodiments, the parallel wall of the flange may have a length that is sufficient to allow for twisting engagement with a pin on an endoscope body.

In other embodiments, the adaptor body may include a flared extension extending beyond one of the ends of the adaptor body. The flared extension may be shaped specifically to facilitate attachment of the adaptor to a water source connector. For example, a water source connector may include an aperture or other opening for receiving a pin in a twisting engagement. Thus, the flared extension may have an exterior surface with at least one pin extending therefrom.

In certain embodiments, the adaptor further may be described as having a first fluid transport channel and a second fluid transport channel. As used herein, the term "fluid" is intended to encompass any material that may be described in relation to flow, such as a gas or a liquid, including solutions or other physical forms of a liquid or a gas that may include some concentration of a solid material in a dissolved, suspended, or otherwise mixed state that does not prevent flow of the liquid or gas. Although the adaptor may be discussed and illustrated in terms of a first and a second fluid transport channel, the adaptor is not limited to only two such channels. Rather, the adaptor could include further fluid transport channels for use with devices where three or more fluids may be transported through a common carrier (e.g., a liquid and two or more gases, a gas and two or more liquids, or two or more gases and two or more liquids). Preferably, each fluid transport channel is a separate, independent channel. In other words, the separate channels do not interconnect, and a fluid in one channel may not be passed into another channel.

The first and second fluid transport channels may be described as being tubes or having a tubular shape. Thus, the fluid transport channels may have walls that delineate the fluid transport area (inside the walls) from the area exterior to the fluid transport channels. The channels or tubes can bridge the two ends of the adaptor body and thus be suspended within the adaptor body. Alternately, one or more of the fluid transport channels may share a wall with the wall of the adaptor. Thus, a portion of one of the channels may form a portion of the wall of the cylindrical body. In other embodiments, one or more of the channels may even be formed so that they are entirely within the wall of the cylindrical body. In specific embodiments, the fluid transport channels are substantially parallel. Preferably, the channels are arranged in a side-by-side arrangement. Of course, the invention also encompasses other arrangements of the fluid transport channels.

The interior of the adaptor body (wherein the fluid transport channels may be located) can be solid or can be open. Preferably, to reduce costs, the interior of the adaptor body is open, and at least one channel is positioned within the adaptor body such that the walls of the channel are not in physical contact with the walls of the adaptor body and/or the walls of another channel. Such open arrangement may be maintained, however, in embodiments wherein the wall of one or more channels may be integral with the wall of another channel and/or with the wall of the cylindrical body of the adaptor.

The adaptor also can comprise an inlet port. The inlet port can be any element extending outward from the exterior surface of an adaptor body and being in fluid connection with at least one fluid transport channel within the adaptor body. The inlet port also can be described as being a substantially tubular shaped element and/or as forming a channel that intersects one of the previously described fluid transport channels formed in the adaptor body. The inlet port particularly can be the element that allows for introduction of a secondary gas, as more particularly described below.

The structure and function of the inventive adaptor are further seen in relation to the various Figures. For example, FIG. 3 illustrates an adaptor 10 according to the invention. The adaptor 10 in FIG. 3 comprises a substantially cylindrical body 12 that essentially forms the core of the adaptor. The adaptor body 12 can be formed of a body wall 14 and can include two closed ends 16 and 18, as shown in FIGS. 3 and 8. The wall 14 of the adaptor body 12 can terminate at the closed ends 16 and 18. Alternately, as seen in FIG. 3, the wall 14 of the adaptor body 12 can extend some distance beyond the closed end 16.

The adaptor 10 further comprises a first fluid transport channel 20 and a second fluid transport channel 30. Although more clearly illustrated in further figures described herein, the fluid transport channels extend from one closed end of the adaptor body to the opposing closed end of the adaptor and have openings at both ends. In such embodiments, the interior of the adaptor body 12 is closed such that fluid passes only through the defined channels and does not contact the interior surface of the adaptor body. In some embodiments, the adaptor body 12 may be described as including a sealed chamber, and the fluid transport channels may extend through the sealed chamber. Alternately, the cylindrical body of the adaptor may be substantially solid, and the channels may form the only open space with the adaptor body.

It is understood that the terms "first" and "second" when used in relation to the fluid transport channels are meant for ease of understanding and are not intended to limit the invention. For example, in FIG. 3, the channel 20 with an opening position approximately in the center of the closed end 16 is described as the first fluid transport channel. In other embodiments, the channel with an opening that is off-center of the closed end 16 of the adaptor 10 could be described as the first fluid transport channel.

The inventive adaptor 10 also comprises an inlet port 40 that extends outward from the wall 14 of the adaptor body 12. The gas inlet port 40 may take on a variety of structures and can have any structure or take on any form suitable to carry out the intended function, which is to provide a port for inputting a secondary gas into the device. In practice, a secondary gas often may be provided via some type of tubing that may or may not include a specialized connection unit (e.g., a screw-on connection or a plug-in connection). For example, the gas inlet port 40 could include a barb, thread, tapered, conical, or snap fitting connection. Thus, the gas inlet port 40 may be designed to accommodate such a specialized connection. In one embodiment, the tubing may be coupled between the gas inlet port 40 and an insufflator unit inputting the secondary gas. In another embodiment, the adapter 10 may also or alternatively include an adhesive for coupling the inlet port 40 to a connection associated with the secondary gas source. Regardless of the type of connection that is to be accommodated, the gas inlet port 40 can comprise a central passage 42 that passes through the wall 14 of the adaptor body 12. The central passage 42 of the gas inlet port 40 preferably intersects the fluid transport channel that functions as a gas transport channel. For example, in FIG. 3, the second fluid transport channel 30 can be referred to as a gas transport channel 30, and the first fluid transport channel 20 can be referred to a liquid transport channel 20. Thus, the positioning of the fluid transport channels within the adaptor body 12 can be important to facilitate proper functioning of the adaptor. Specifically, as shown in the embodiment of FIG. 3, the liquid transport channel 20 is centralized within the adaptor body 12, and the gas transport channel is off-set toward the wall 14 of the adaptor body 12. This positioning facilitates ease of interaction between the central passage 42 in the gas inlet port 40 and the gas transport channel 30. In particular, the central passage 42 can be in fluid connection with the gas transport channel 30 such that the central passage 42 extends and opens into the gas transport channel 30. Such central passage 42 can be solely for passage of the secondary gas or also can form an entry port for insertion of a gas connection. For example, if the gas is to be provided via a device having a specialized plug-in connector, the passage 42 can be formed to accommodate the plug. Thus, the passage 42 can be described as being an annular passage with walls that may have formed therein specialized components (e.g., grooves or threads) for receiving a plug. The components particularly may allow for removable attachment of a plug device for delivery of gas.

In specific embodiments, the gas inlet port 40 may substantially extend outward from the wall 14 of the adaptor body 12 at a position that is substantially close in position to the gas transport channel 30. Such a structure particularly is useful to accommodate attachment of a gas line having a screw-on component or a gas line that attaches by simply being pressed over and onto the extending portion of the port 40 (e.g., a standard, flexible hose or tube).

In one embodiment, the gas inlet port 40 may comprise a luer connector or any similar structure. Luer connection systems typically are associated with the interconnection of syringes, catheters, hubbed needles, IV tubes, and the like. A luer connection system consists of round male and female interlocking tubes that may be slightly tapered to hold together better with even just a simple pressure/twist fit. As illustrated in FIG. 3, the luer connector is a female component. In use, a male luer connector may simply slip inside the shown female component and form a secure connection. The illustrated embodiment provides for an even more secure fit through inclusion of an additional outer rim 44 (which functions as a single thread). As shown, the rim 44 is formed of two separate "wings." In use, the male luer connector can include an additional outer rim of threading to form a "locked" connection.

The liquid transport channel 20 and the gas transport channel 30 each open to the environment at the closed end 16 of the adaptor body 12. Although not visible in FIG. 3, both channels likewise open to the environment at the closed end 18 of the adaptor body. In the embodiment of FIG. 3, the visible closed end can be referred to as the first closed end 16. Specifically, the first closed end 16 may be structured and designed for attachment to an endoscope device. For example, the wall 21 of the liquid transport channel 20 may extend beyond the first closed end 16. Similarly, the wall 14 of the adaptor body 12 may extend beyond the first closed end 16. Such arrangement may provide a topographical structure the particularly facilitates a sealed engagement with a fluid transport element on an endoscope device.

Additionally, the inventive adaptor 10 may comprise a flange 110 that is attached to the wall 14 of the adaptor body 12 in the proximity of the first closed end 16. The flange 110 particularly can include a flange wall 115 that is substantially parallel to the wall 14 of the adaptor body 12. The flange with its wall may be referred to herein as a stationary sleeve. As seen in FIG. 3, the flange with the wall forms a component that substantially completely surrounds the first closed end 16. As described further below, this provides means for engaging the adaptor 10 with the main body of an endoscope device. To this end, the flange wall 115 can include means for receiving an extension, such as a pin, present on the endoscope device to secure the adaptor 10 to the endoscope. As illustrated in FIG. 3, the means comprise two receiving channels 120 formed in the flange wall 115. Of course, any means useful to receive an extension, such as a pin, could be used. Specifically, the means could be a groove, aperture, or generally any opening that will allow an extension from the endoscope to interact with the inventive adaptor to secure the two devices together. In FIG. 3, the receiving channels 120 are formed with an angled portion 122 and a horizontal portion 124. Preferably, the horizontal portion 124 comprises one or more locking teeth 125 that are useful to resist any twisting movement of the adaptor 10 once attached to the endoscope. In this embodiment, the adaptor 10 can attach to an endoscope by aligning the pins on the endoscope with the receiving channels 120 and pressing the adaptor 10 toward the pins while twisting to cause the pins to slide through the angled portion 122 and into the horizontal portion 124 with the pins can engage the locking teeth 125.

Similar to the above, the second closed end 18 of the adaptor 10 may be structured and designed for attachment to a water source connector. For example, the adaptor body wall 14 may comprise a flared extension 130, and this extension 130 may extend beyond the second closed end 18. In particular embodiments, the flared extension 130 can comprise an exterior surface with at least one pin 135 extending therefrom. The flared extension and the associated pin can facilitate connection of the second end of the adaptor to a water source connector, particularly a connector including one or more channels for receiving a pin as a connection and/or locking mechanism.

An adaptor according to certain embodiments of the invention also is shown in FIG. 4 as a bottom view (i.e., looking directly at the gas inlet port 40). A top view of the adaptor 10 is shown in FIG. 5. As seen in this embodiment, the gas inlet port 40 can be formed to be substantially perpendicular to the exterior surface of the adaptor body 12. The fluid connection between the gas inlet port 40 and the gas transport channel 30 is also seen in FIG. 4. Specifically, the figure shows the central passage 42 of the gas inlet port 40 opening into the gas transport channel 30 via an opening in the wall 14 of the adaptor body 12. Thus, the central passage 42 can be viewed as being separate from the gas transport channel 30 or can be viewed as being a branch of the gas transport channel 30.

As seen in the embodiment of FIG. 4, the external surfaces of the various areas of the inventive adaptor 10 may have different relative dimensions. In one embodiment, as illustrated, the various areas are all substantially cylindrical in shape. For example, the adaptor body 12 may have an outside diameter that is less than the outside diameter of the flared extension 130, and the flange 110 may have an outside diameter that is less than the outside diameter of one or both of the adaptor body 12 and the flared extension 130. The dimensions of the various components may be designed specifically to facilitate attachment of the adaptor to an endoscope and/or a water supply connector. The overall length of the various areas of the adaptor also may have differing dimensions. For example, the length of the adaptor body 12 can be greater than the length of the flange 110 and the flared extension 130.

In some embodiments, the inventive adaptor may have an overall length of about 1.5 cm to about 8 cm. Even greater overall lengths are encompassed by the present invention; however, such greater lengths would be expected to add only to the cost and not the function of the adaptor and thus, are not necessarily preferred. In other embodiments, the adaptor may have an overall length of about 2 cm to about 7 cm, about 2 cm to about 6 cm, about 2 cm to about 5 cm, about 2 cm to about 4 cm, or about 2 cm to about 3 cm.

Front and rear views of an adaptor 10 according to the invention are shown in FIG. 6 and FIG. 7, respectively. For ease of description, the end of the adaptor structured and designed for attachment to an endoscope is referred to as the front, and the end of the adaptor structure and designed for attachment to a water source connector is referred to as the rear of the adaptor. Such terms are not to be construed as limiting.

The adaptor of the invention may include further components in addition to those already described. Such further components may be separate from the monolithic structure of the adaptor. Such further components may be formed separately from the monolithic structure of the adaptor but may be combined with the adaptor in such a manner so as to effectively become an integral part of the overall structure.

In certain embodiments, such as illustrated in FIG. 8, the adaptor 10 further may comprise one or more sealing members. As illustrated, a gasket 200 is included and is sized appropriately to be place in the flared extension 130 at the second closed end 18. The gasket includes two openings that correspond to the openings formed in the second closed end 18 by the first fluid transport channel 20 and the second fluid transport channel 30. Of course, other types of sealing members are encompassed by the invention. As further described below, the sealing member is useful for forming a fluid-tight connection between the adaptor and the devices to which it is attached. The sealing member can be retained in contact with the second closed end by any appropriate means including gluing or simply sizing the gasket so that the edges thereof contact the inner surface of the flared extension and maintain placement by friction alone. The flared extension likewise could include a groove, lip, or other structural member useful to maintain the sealing member in its position.

The overall structure of an adaptor 10 according to one embodiment of the invention particularly is illustrated in the cross-section provided in FIG. 9. As seen therein, the adaptor 10 can be described as being a single, unitary structure with a number of channels formed therein. Specifically, the first fluid transport channel 20 and the second fluid transport channel 30 are seen to both extend from the first closed end 16 of the adaptor body 12 to the second closed end 18 of the adaptor body 12. Further, the intersection of the second fluid transport channel 30 and the central passage 42 of the gas inlet port 40 is illustrated. In the embodiment shown in FIG. 9, the body 12 of the adaptor 10 is a solid piece with the channels 20 and 30 formed therein. In other embodiments, the body of the adaptor may be substantially hollow such that the walls of the channel 20 and optionally the channel 30 are distinguishable inside the body of the adaptor and exist within the walls 14 of the adaptor body 12.

The adaptor of the invention can be made of a variety of different materials, which may affect how the adaptor is formed. In certain embodiments, the adaptor may be a machined part. As such, the adaptor particularly may comprise a plurality of individual parts that are machined separately and then combined to form the final adaptor assembly. Such combination can be by any means recognized as useful in the art, such as gluing, welding or the like or using further attachment components, such as rivets, or the like.

In preferred embodiments, the inventive adaptor may be a molded part. This particularly is advantageous for providing the adaptor as a single, monolithic structure, which provides for a seamless construction. In embodiments where the adaptor is reusable, this simplifies cleaning and ensures no contaminants remain in seams, etc. existing between multiple parts that may be combined to form the adaptor. Thus, the final adaptor can be formed to have no moving parts.

The adaptor of the invention is also beneficial in that it can be provided as a single-use (i.e., disposable) adaptor or may be provided as a reusable adaptor. In some embodiments, the inventive adaptor can be both single-use and reusable in that the end-user will have the option to dispose of the adaptor after a single use or sterilize the adaptor and reuse it. This is achievable in particular because of the ability to form the adaptor from a variety of materials using a variety of methods. Thus, the adaptor can be sufficiently economical to justify making only a single use to avoid the need to sterilize. At the same time, the adaptor can be sufficiently sturdy to withstand multiple sterilization procedures.

The adaptor can be formed from a variety of different materials. In some embodiments, the adaptor comprises a metal material. Preferably, the metal is non-corrosive (e.g., stainless steel or aluminum). In other embodiments, the adaptor comprises a polymeric material, which preferably is chemical resistant, heat resistant, or both chemical resistant and heat resistant. The use of medical grade plastic materials is particularly desirable. In one specific embodiment, the polymeric material is a polysulfone (e.g., polyphenylsulfone) or a similar material. Non-limiting examples of further polymeric materials that may be used to form one or more component of the inventive adaptor include polyethylene (e.g., UHME-PE), polypropylene, polymethylmethacrylate (PMMA), acetal copolymers, polythermide, polycarbonate, and polyetheretherketone (PEEK). The sealing members can be formed of any material recognized as useful in forming such elements, such as natural or synthetic rubbers.

In one embodiment, the adaptor of the invention can comprise a single plastic component and one gasket. The plastic component can be the adaptor body with two, opposing closed ends, and can include a liquid channel and a gas channel, each channel extending through the adaptor body and opening to the exterior at the opposing ends of the adaptor body. The adaptor also can include a gas inlet that intersects the gas channel and preferably is substantially perpendicular to the liquid channel and the gas channel. Thus, the gas channel can open to the exterior at three points. The gasket can be located at one end of the adaptor body. Preferably, one end of the adaptor body comprises a flared portion, and the gasket can be located within the flared portion against the body end.

The adaptor of the invention is particularly useful in light of the specific design thereof that enables the adaptor to be inserted in-line with a known endoscopic device. This is particularly illustrated in FIG. 10, FIG. 11, and FIG. 12.

More particularly, the adaptor of the invention can be formed for specific use with an endoscopic device from a particular manufacturer. As pointed out previously, typical endoscopic devices include a control body that connects to a variety of components; however, the connection means vary based upon the manufacturer.

Accordingly, in one embodiment, an adaptor according to the present invention can be specifically designed and shaped for attachment to a Fujinon-manufactured endoscopic device. More particularly, the adaptor can be designed and shaped for insertion in-line between a water source connector and a control body of a Fujinon OEM endoscope (i.e., an original equipment manufacturer endoscope manufactured by Fujinon Corporation).

The ability of the adaptor to be used in-line with an existing endoscopic device is seen in FIG. 10, where the inventive adaptor 10 is positioned to be attached at one end to an endoscope control body 300 and at the other end to a water source connector 400. The control body 300 includes a fluid source hub 310, and the hub includes at least one pin 315 extending from a portion thereof. In typical use, the pin 315 engages a receptacle 410 in the water source connector 400 in a twisting motion to lock the two components together. The first end 16 of the adaptor 10 can be designed and shaped to engage the fluid source hub 310 in a similar twisting fashion to lock the adaptor to the endoscope control body 300. Specifically, the inventive adaptor 10 can engage the fluid source hub 310 such that the walls 115 of the flange 110 fit over and around the hub 310, and the wall of the hub 310 slides between the walls 115 of the flange 110 and the wall 14 of the adaptor body 12 that extend beyond the first closed end 16 of the adaptor 10. Upon attachment, the pin 315 on the hub 310 slides into the receiving channel 120 formed in the wall 115 of the adaptor flange 110. By pressing the adaptor 10 toward the pin 315 while twisting, the pin slides through the angled portion 122 and into the horizontal portion 124 of the receiving channel 120. At this point, the pins can engage the locking teeth 125 to prevent undesired disengagement. Preferably, the receiving channel 120 of the inventive adaptor 10 is positioned on the flange wall 115 such that in a fully engaged position, the liquid transport channel 20 aligns with a liquid receptacle on the endoscope control body 300 and the gas transport channel 30 aligns with a gas receptacle on the endoscope control body 300. As inventive adaptor is designed and shaped to engage the fluid source hub on the endoscope control body, the inventive adaptor can be described as including a portion that is substantially identical in shape and dimension to the engaging portion of a water source connector. Specifically, the portion of the adaptor in proximity to the first end of the adaptor may be designed and shaped to be substantially identical in shape and dimension to the engaging portion of the water source connector.

Similarly, the second end 18 of the adaptor 10 can be designed and shaped to connect to the engaging portion of the water source connector 400. A typical water source connector designed to engage the control body on an endoscope body manufactured by Fujinon Corporation includes a sleeve surrounding a central cylinder with an annular space therebetween for receiving the wall of the fluid source hub 310. Thus, in specific embodiments, the second end 18 of the inventive adaptor 10 can be described as including a flared portion 130 with a rim that is shaped and structured to engage the annulus of a water source connector. Specifically, the rim can include one or more pins 135 that engage a channel formed in the sleeve of the water source connector to secure the engagement of the two components. In particular embodiments, the inventive adaptor 10 can be described as including an end that is substantially identical in shape and dimension to a portion of the fluid source hub formed on the endoscope control body for attachment to the water source connector.

The inventive adaptor particularly is advantageous in that it can be used simply as a press-fit device. Specifically, the adaptor can be designed to allow for being press-fit into engagement with the remaining components, as described above. The use of a twisting motion to secure the press-fit engagement does not limit this description since the engagement and securing of the components can be achieved without the use of any secondary engaging means (e.g., in the express absence of a screw collar or the like).

The inventive adaptor 10 is shown in FIG. 11 fully engaging the endoscope control body 300 and the water source connector 400. As seen in FIG. 11, the gas inlet 40 on the adaptor 10 is positioned in this engagement for ready attachment to a secondary gas source, such as a $CO_2$EFFICIENT Endoscopic Insufflator.

The engagement of the inventive adaptor with the endoscope control body and the water source connector is more readily evident in the cross-section provided in FIG. 12. As seen therein, the liquid transport channel 20 aligns with a liquid transport channel 320 in the endoscope control body 300 and with a liquid transport channel in the water source connector 400. Further, the rim of the fluid source hub 310 on the endoscope control body 300 is engaging the annulus space between the wall 14 of the first end of the adaptor body 12 and the wall 115 of the flange 110. Likewise, the flared extension 130 on the second end of the adaptor 10 is engaging the water source connector 400, and the pins 135 on the flared end 130 are positioned within the channels formed in the outer portion of the water source connector 400.

In specific embodiments, it is possible for the adaptor of the invention to be attached to the endoscope control body and the water source connector in different orientations. FIG. 12 illustrates a single orientation. In alternate embodiments, the endoscope control body could be rotated 180° relative to the axis formed along the line of connection between the endoscope control body, the inventive adaptor, and the water source connector. Likewise, in other embodiments, the water source connector could be rotated 180° around the same axis. In the possible orientations for the connection of the endoscope body with the inventive adaptor, gas flow from the adaptor to the endoscope body can be made possible regardless of the alignment between the gas transport channel in the adaptor and any gas transport means provided in the endoscope body. For example, the inventive adaptor may be formed such that there is a sealed pocket formed between the interface of the adaptor and endoscope main body. In specific embodiments, the seal is formed by a gasket that can be present as part of the endoscope main body. This gasket can be substantially similar to the gasket that is provided on the opposing end of the inventive adaptor for creating a seal between the adaptor and the water source connector. The gasket preferably is effective to create a sealed area or compartment wherein gas can flow freely between the adaptor and the endoscope body. Preferably, the sealed compartment allows for gas flow between the end of the adaptor and the endoscope body while preventing flow of the gas into any liquid channel formed in the endo scope body for receiving liquid that is transported through the inventive adaptor. The structure is beneficial in that it facilitates gas flow regardless of how the user connects the adaptor to the endoscope body. Thus, the adaptor can be described as being attachable to the endoscope body independent of the orientation of the adaptor with respect to the endoscope body.

In light of the foregoing, it can be seen that, in certain embodiments, the adaptor of the invention can comprise a cylinder with a wall, two opposing, closed ends, an inlet port extending outward from the cylinder, and at least two channels formed on the interior of the cylinder, extending the length of the cylinder, and opening at both ends of the cylinder. One end of the cylinder can include a stationary sleeve that forms an open annulus between the sleeve and the cylinder wall. The sleeve can include one or more receiving channels that will receive a pin in a twisting motion. The other end can include a flared wall extending beyond the cylinder end. The flared wall can include a pin that will engage a receiving channel in a twisting motion. Preferably, the inlet port includes a passage that opens through the cylinder wall and intersects one of the channels formed on the interior of the cylinder.

In other aspects, the present invention also provides various methods that make use of the inventive adaptor. For example, the invention can be directed to methods of performing an endoscopic procedure. In one embodiment, the method can comprise using an assembly that includes an endoscopic device, a water source, a gas source, and an adaptor according to any of the embodiments described herein. In other words, the inventive adaptor could be combined at the point of use with an OEM endoscope, particularly an endoscope having a fluid transport hub that engage a receptacle in a water source connector, such as an endoscope manufactured by Fujinon Corporation.

As previously noted, the present invention is particularly beneficial in that it allows for the easy and efficient delivery of a secondary gas to an endoscope. Thus, in other aspects, the present invention also can be directed to methods for supplying a secondary gas in an endoscopic procedure. In certain embodiments, the method can comprise using an endoscope device having attached thereto a water source with a connector. Particularly, the endoscope device can have a fluid transport hub that engages a receptacle in the water source connector. The method further can comprise using an adaptor according to any embodiment of the present invention. In particular, the method can comprise affixing between the water source connector and the endoscope device an adaptor according to the present invention and supplying a secondary gas to the endoscope device via the gas inlet port on the adaptor. Although any gas suitable for use in medical or veterinary procedures could be supplied, in particular embodiments, the secondary gas can comprise carbon dioxide.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An adaptor for an endoscopic device, the adaptor comprising:
    a body having a wall, a first closed end, and a second, opposing closed end;
    a first fluid transport channel having a channel wall and extending through the body and opening at the first closed end and the second closed end;
    a second fluid transport channel having a channel wall and extending through the body and opening at the first closed end and the second closed end; and
    an inlet port extending outward from the wall of the body and having a central passage extending through the wall of the body and being in fluid and physical connection with the first or second fluid transport channel,
    wherein the adaptor is configured to be attached in-line between an endoscopic device and a first fluid source connector such that the first and second fluid transport channels are in fluid connection with the endoscopic device and the first fluid source connector,
    wherein the inlet port is configured to receive a secondary fluid source for providing to the endoscopic device,
    wherein the body comprises a first connecting portion in the proximity of the first closed end and a second connecting portion in the proximity of the second closed end,
    wherein the first connecting portion is configured to be interlocked with a third connecting portion that is substantially identical to the second connecting portion.

2. The adaptor of claim 1, wherein the first connecting portion comprises a flange in the proximity of the first closed end.

3. The adaptor of claim 2, wherein the flange comprises a flange wall that is substantially parallel to the wall of the body.

4. The adaptor of claim 3, wherein the flange wall comprises means for receiving a pin in a sliding engagement.

5. The adaptor of claim 2, wherein the second connecting portion comprises a flared extension of the body wall extending beyond the second closed end.

6. The adaptor of claim 5, wherein the flared extension comprises an exterior surface with at least one pin extending therefrom.

7. The adaptor of claim 1, further comprising a sealing member located at an exterior surface of one or both of the first and second closed ends.

8. The adaptor of claim 1, wherein the inlet port is substantially perpendicular to the wall of the body.

9. The adaptor of claim 1, wherein the adaptor is a single, monolithic structure.

10. The adaptor of claim 1, wherein the adaptor is shaped in the proximity of the first closed end to engage a fluid transport element extending from a portion of the endoscopic device.

11. The adaptor of claim 1, wherein the first and second fluid transport channels are substantially parallel.

12. The adaptor of claim 1, wherein the first fluid transport channel is a liquid channel, the second fluid transport channel is a gas channel, the central passage in the inlet port is in fluid connection with the gas channel, the first fluid source connector is a water source connector, and the secondary fluid source is a secondary gas source.

13. The adaptor of claim 12, wherein a portion of the gas channel forms a portion of the body wall.

14. The adaptor of claim 12, wherein the gas channel is formed within the body wall.

15. The adaptor of claim 12, further comprising a tubing coupled between the inlet port and an insufflator unit for supplying the secondary gas source to the second fluid transport channel.

16. An adaptor for an endoscopic device, the adaptor comprising:
    a body having a wall, a first closed end, and a second, opposing closed end;
    a first fluid transport channel having a channel wall and extending through the body and opening at the first closed end and the second closed end;
    a second fluid transport channel having a channel wall and extending through the body and opening at the first closed end and the second closed end; and
    an inlet port extending outward from the wall of the body and having a central passage extending through the wall of the body and being in fluid and physical connection with the first or second fluid transport channel,
    wherein the first closed end comprises a first connecting portion, wherein the second closed end comprises a second connecting portion,
    wherein the first connecting portion is configured to be interlocked with a third connecting portion which is substantially identical to the second connecting portion.

* * * * *